United States Patent
Anderson et al.

(10) Patent No.: US 9,168,307 B2
(45) Date of Patent: Oct. 27, 2015

(54) MITOCHONDRIAL-TARGETED CATIONIC NANOPARTICLES COMPRISING CAMKII INHIBITORS AND USES THEREOF FOR TREATING AND PREVENTING DISEASES AND DISORDERS ASSOCIATED WITH CAMKII ACTIVITY

(71) Applicant: University of Iowa Research Foundation, Iowa City, IA (US)

(72) Inventors: Mark E. Anderson, Iowa City, IA (US); Mei-ling A. Joiner, Iowa City, IA (US); Aliasger K. Salem, Coralville, IA (US); Amaraporn Wongrakpanich, Iowa City, IA (US); Frederick E. Domann, Iowa City, IA (US); Duane D. Hall, Cedar Rapids, IA (US); Olha M. Koval, Iowa City, IA (US); Douglas R. Spitz, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 89 days.

(21) Appl. No.: 14/017,847

(22) Filed: Sep. 4, 2013

(65) Prior Publication Data
US 2014/0066388 A1 Mar. 6, 2014

Related U.S. Application Data

(60) Provisional application No. 61/696,631, filed on Sep. 4, 2012.

(51) Int. Cl.
*A61K 47/42* (2006.01)
*A61K 9/51* (2006.01)
*A61K 47/48* (2006.01)
*A61K 38/17* (2006.01)

(52) U.S. Cl.
CPC ............... *A61K 47/42* (2013.01); *A61K 9/5123* (2013.01); *A61K 9/5146* (2013.01); *A61K 9/5153* (2013.01); *A61K 38/1709* (2013.01); *A61K 47/48238* (2013.01); *A61K 47/48907* (2013.01); *A61K 47/48915* (2013.01)

(58) Field of Classification Search
CPC ..... A61K 47/42; A61K 47/48; A61K 9/5123; A61K 9/5146; A61K 9/5153; A61K 38/1709; A61K 2300/00; A61K 47/48238; A61K 47/48907; A61K 47/48915
See application file for complete search history.

(56) References Cited

FOREIGN PATENT DOCUMENTS

WO WO 2009047587 A1 * 4/2009 ........... C01N 33/543

OTHER PUBLICATIONS

V. Bhardwaj, PLGA Nanoparticles Stabilized with Cationic Surfactant: Safety Studies and Application in Oral Delivery of Paclitaxel to Treat Chemical-Induced Breast Cancer in Rat, Pharmaceutical Research, vol. 26, No. 11, Nov. 2009.*
Mei-ling Joiner, Mitochondrial CaMKII couples Ca2+ and ROS to metabolism and cell death in the heart, University of Iowa, Power point presentation, 2010.*
Calcium Calmodulin dependent protein kinase inhibitor II inhibitor 2, Q96S95 accession No. UniProtKB/Swiss-Prot, Dec. 1, 2001.*
Abbas et al., "Formulating Poly (lactide-co-glycolide) Particles for Plasmid DNA Delivery", Journal of Pharmaceutical Sciences, 2008, 97(7): 2448-2461.
Boddapati et al., "Organelle-targeted Nanocarriers: Specific Delivery of Liposomal Ceramide to Mitochondria Enhances its Cytotoxicity In Vitro and In Vivo", Nano Letters, 2008, 8(8): 2559-63.
Boddapati et al., "Liposomes for Drug Delivery to Mitochondria", Methods Mol Biol, 2010, 605: 295-303.
Clapper et al., "Biotinylated Biodegradable Nanotemplated Hydrogel Networks for Cell Interactive Applications", Biomacromolecules, 2008, 9(4):1188-94.
Halestrap, A.P., "What is the Mitochondrial Permeability Transition Pore?", Journal of Molecular and Cellular Cardiology, 2009, 46(6): 821-831.
Intra et al., "Rational Design, Fabrication, Characterization and In Vitro Testing of Biodegradable Microparticles that Generate Targeted and Sustained Transgene Expression in HepG2 Liver Cells", Journal of Drug Targeting, 2011, 19 (6): 393-408.
Joshi et al., "Characterizing the Antitumor Response in Mice Treated with Antigen-Loaded Polyanhydride Microparticles", Acta Biomater, 2013, 9(3): 5583-9.
Krishnamachari et al., "Self-Assembly of Cell-Microparticle Hybrids", Advanced Materials, 2008, 20(5): 989-+.
Kroemer et al., "Mitochondrial Control of Cell Death", Nature Medicine, 2000, 6(5): 513-519.
Lemke et al., "Antigen-Coated Poly Alpha-Hydroxy Acid Based Microparticles for Heterologous Prime-Boost Adenovirus Based Vaccinations", Biomaterials, 2013, 34(10): 2524-9.
Miyawaki et al., "Fluorescent Indicators for Ca2+Based on Green Fluorescent Proteins and Calmodulin", Nature, 1997, 388(6645): 882-887.
Odagiri et al., "Local Control of Mitochondrial Membrane Potential, Permeability Transition Pore and Reactive Oxygen Species by Calcium and Calmodulin in Rat Ventricular Myocytes", Journal of Molecular and Cellular Cardiology, 2009, 46(6): 989-997.
Petushkov et al., "Effect of Crystal Size and Surface Functionalization on the Cytotoxicity of Silicalite-1 Nanoparticles", Chemical Research in Toxicology, 2009, 22(7): 1359-1368.
Salem et al., "Synthesis and Characterisation of a Degradable Poly(lactic acid)-Poly(ethylene glycol) Copolymer with Biotinylated End Groups", Biomacromolecules, 2001, 2(2): 575-580.
Salem et al., "Porous Polymer and Cell Composites that Self-Assemble in Situ", Advanced Materials, 2003, 15(3): 210.
Salem et al., "Multifunctional Nanorods for Gene Delivery", Nature Materials, 2003, 2(10): 668-671.

(Continued)

Primary Examiner — James H Alstrum Acevedo
Assistant Examiner — Erinne Dabkowski
(74) Attorney, Agent, or Firm — Andrus Intellectual Property Law, LLP

(57) ABSTRACT

Disclosed are compositions and methods for treating or preventing diseases or disorders associated with mitochondrial CaMKII activity.

11 Claims, 9 Drawing Sheets

(56) References Cited

OTHER PUBLICATIONS

Salem et al., "Receptor-Mediated Self-Assembly of Multi-Component Magnetic Nanowires", Advanced Materials, 2004, 16(3): 268-+.
Sinclair et al., "Rapid Localized Cell Trapping on Biodegradable Polymers Using Cell Surface Derivatization and Microfluidic Networking", Biomaterials, 2006, 27(9): 2090-4.
Zhang et al., "A Comparative Study of the Antigen-Specific Immune Response Induced by Co-Delivery of CpG ODN and Antigen using Fusion Molecules or Biodegradable Microparticles", J Pharm Sci, 2007, 96(12): 3283-92.
Zhang et al., "Conjugation of Polyamidoamine Dendrimers on Biodegradable Microparticles for Nonviral Gene Delivery", Bioconjugate Chemistry, 2007, 18(6): 2068-2076.
Zhang et al., "Comparative Study of Poly (lactic-co-glycolic acid)-Poly Ethyleneimine-Plasmid DNA Microparticles Prepared using Double Emulsion Methods", Journal of Microencapsulation, 2008, 25(1): 1-12.
Zordoky et al., "H9c2 Cell Line is a Valuable In Vitro Model to Study the Drug Metabolizing Enzymes in the Heart, Journal of Pharmacological and Toxicological Methods", 2007, 56(3): 317-322.
Baughman et al., "Integrative genomics identifies MCU as an essential component of the mitochondrial calcium uniporter", Nature, 2011, 476(7360): 341-5.
Biswas et al., "Surface conjugation of triphenylphosphonium to target poly(amidoamine) dendrimers to mitochondria", Biomaterials, 2012, 33(18): 4773-82.
Chao et al., "Intersubunit capture of regulatory segments is a component of cooperative CaMKII activation", Nat Struct Mol Biol, 2010, 17(3): 264-72.
Clapham, "Calcium Signaling", Cell, 2007, 131(6): 1047-1058.
Coultrap et al., "Improving a natural CaMKII inhibitor by random and rational design", PLoS One, 2011, 6(10): e25245.
Erickson et al., "A dynamic pathway for calcium-independent activation of CaMKII by methionine oxidation", Cell, 2008, 133(3): 462-474.
Hakem et al., "Differential requirement for caspase 9 in apoptotic pathways in vivo", Cell, 1998. 94(3): 339-352.
Hong et al., "Intracellular Release of 17-beta Estradiol from Cationic Polyamidoamine Dendrimer Surface-Modified Poly (Lactic-co-Glycolic Acid) Microparticles Improves Osteogenic Differentiation of Human Mesenchymal Stromal Cells", Tissue Engineering Part C-Methods, 2011, 17(3): 319-325.
Hong et al., "Effects of Glucocorticoid Receptor Small Interfering RNA Delivered Using Poly Lactic-Co-Glycolic Acid Microparticles on Proliferation and Differentiation Capabilities of Human Mesenchymal Stromal Cells", Tissue Engineering Part A, 2012, 18(7-8): 775-784.
Jiang et al., "A mitochondrial-targeted triphenylphosphonium-conjugated nitroxide functions as a radioprotector/mitigator", Radiat Res, 2009, 172(6): 706-17.
Jiang et al., "Optimized dextran-polyethylenimine conjugates are efficient non-viral vectors with reduced cytotoxicity when used in serum containing environments", International Journal of Pharmaceutics, 2012, 427(1): 71-79.
Joiner et al., "CaMKII determines mitochondrial stress responses in heart", Nature, 2012, 491(7423): 269-73.
Kim et al., "Synthesis and characterization of mannosylated pegylated polyethylenimine as a carrier for siRNA", International Journal of Pharmaceutics, 2012, 427(1): 123-133.
Krishnamachari et al., "Innovative strategies for co-delivering antigens and CpG oligonucleotides", Advanced Drug Delivery Reviews, 2009, 61(3): 205-217.
Liu et al., "Ouabain induces endocytosis of plasmalemmal Na/K-ATPase in LLC-PK1 cells by a clathrin-dependent mechanism", Kidney International, 2004, 66(1): 227-241.
Marrache et al., "Engineering of blended nanoparticle platform for delivery of mitochondria-acting therapeutics", Proc Natl Acad Sci U S A, 2012, 109(40): 16288-93.
Olichon et al., "Loss of OPA1 perturbates the mitochondrial inner membrane structure and integrity, leading to cytochrome c release and apoptosis", J. Biol. Chem., 2003, 278(10): 7743-7746.
Sakhalkar et al., "Leukocyte-inspired biodegradable particles that selectively and avidly adhere to inflamed endothelium in vitro and in vivo", Proceedings of the National Academy of Sciences of the United States of America, 2003, 100(26): 15895-15900.
Singh et al., "Ca2+/calmodulin-dependent kinase II triggers cell membrane injury by inducing complement factor B gene expression in the mouse heart", J. Clin. Invest., 2009, 119(4): 986-996.
Tyurina et al., "Mitochondria targeting of non-peroxidizable triphenylphosphonium conjugated oleic acid protects mouse embryonic cells against apoptosis: role of cardiolipin remodeling", FEBS Lett, 2012, 586(3): 235-41.
Walters et al., "Mitochondria as a drug target in ischemic heart disease and cardiomyopathy", Circ Res, 2012, 111 (9): 1222-36.
Yang et al., "Calmodulin kinase II inhibition protects against myocardial cell apoptosis in vivo", Am. J. Physiol, Heart Circ. Physiol., 2006, 291(6): H3065-H3075.
Yoo et al., "Synthesis of the first poly(diaminosulfide)s and an investigation of their applications as drug delivery vehicles", Macromolecules, 2012, 45(2): 688-697.
Zhang et al., "The {delta}C Isoform of CaMKII Is Activated in Cardiac Hypertrophy and Induces Dilated Cardiomyopathy and Heart Failure", Circ Res, 2003, 92(8): 912-919.
Zhang et al., "Calmodulin kinase II inhibition protects against structural heart disease", Nature Medicine, 2005, 11 (43): 409-417.
Zhang et al., "Role of mitochondria in angiotensin II-induced reactive oxygen species and mitogen-activated protein kinase activation", Cardiovasc Res, 2007, 76(2): 204-12.
Pellicena et al., "CaMKII inhibitors: from research tools to therapeutic agents", Frontiers in Pharmacology, Feb. 2014, 5(21):1.
Pfanner, "Protein sorting: Recognizing mitochondrial presequences", Current Biology, 2000, 10:R412-R415.

* cited by examiner

Figure 1.

MLS: MSVLTPLLLRGLTGSARRLPVPRAKIHSLL (SEQ ID NO:2)

CaMKII Inhibitor: KRPPKLGQIGRAKRVVIEDDR (SEQ ID NO:1)

SEQUENCE LISTING

```
<160> NUMBER OF SEQ ID NOS: 2

<210> SEQ ID NO 1
<211> LENGTH: 21
<212> TYPE: PRT
<213> ORGANISM: Artificial
<220> FEATURE:
<223> OTHER INFORMATION: Peptide inhibor of human CaMKII derived from
      human CaMKIIN

<400> SEQUENCE: 1

Lys Arg Pro Pro Lys Leu Gly Gln Ile Gly Arg Ala Lys Arg Val Val
1               5                   10                  15

Ile Glu Asp Asp Arg
            20

<210> SEQ ID NO 2
<211> LENGTH: 30
<212> TYPE: PRT
<213> ORGANISM: Homo sapiens

<400> SEQUENCE: 2

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Leu
            20                  25                  30
```

MITOCHONDRIAL-TARGETED CATIONIC NANOPARTICLES COMPRISING CAMKII INHIBITORS AND USES THEREOF FOR TREATING AND PREVENTING DISEASES AND DISORDERS ASSOCIATED WITH CAMKII ACTIVITY

CROSS-REFERENCE TO RELATED APPLICATIONS

The present application claims the benefit of priority under 35 U.S.C. §119(e) to U.S. Provisional Patent Application No. 61/696,631, filed on Sep. 4, 2012, the content of which is incorporated herein by reference in its entirety.

STATEMENT REGARDING GOVERNMENT SPONSORED RESEARCH OR DEVELOPMENT

This invention was made with government support under Grant No. R01HL070250 awarded by the National Institutes of Health, Heart, Lung, and Blood Institute. The Government has certain rights in this invention.

BACKGROUND

The field of the invention relates to treatment of diseases and disorders associated with calcium/calmodulin dependent protein kinase II (CaMKII) activity. In particular the field of the invention relates to inhibition of mitochondrial CaMKII activity for treatment of diseases and disorders associated with mitochondrial CaMKII activity.

Mitochondria are structurally dynamic organelles which are known to initiate cell death. Myocardial-initiated cell death is caused by excess mitochondrial $Ca^{2+}$ entry, leading to $Ca^{2+}$ overload, mitochondrial permeability transition pore (mPTP) opening and dissipation of the mitochondrial inner membrane potential ($\Delta\Psi m$). The multifunctional $Ca^{2+}$ and calmodulin-dependent protein kinase II (CaMKII) is activated in ischemia reperfusion FR), myocardial infarction (MI) and neurohumoral injury which are all common causes of myocardial death and heart failure. This indicates that CaMKII links disease stress to mitochondrial injury. We recently reported that CaMKII promotes mPTP opening and myocardial death by increasing mitochondrial calcium uniporter (MCU) current ($I_{MCU}$) (See Joiner et al. Nature, 2012. 491(7423):p. 269-73; and U.S. Provisional Patent Application No. 61/696,631). Mitochondrial-targeted CaMKII inhibitory protein, an mPTP antagonist with clinical efficacy in I/R injury, prevent mPTP opening, $\Delta\Psi m$ deterioration and diminishes mitochondrial disruption and programmed cell death in response to I/R injury. These findings identify CaMKII activity as a central component in the mechanism for mitochondrial $Ca^{2+}$ entry and suggest mitochondrial-targeted CaMKII inhibition can prevent or reduce myocardial death and heart failure dysfunction in response to common experimental forms of pathophysiological stress.

Here, we disclose new mitochondrial-targeted reagents and a therapeutic strategy to treat or prevent mitochondria triggered cell death linked to over-activation of mitochondria via CaMKII activation of the MCU. The disclosed reagents will have broad application, not only to prevent or reduce myocardial death and heart failure dysfunction but also to other treat or prevent other diseases and disorders. This is because mitochondrial dysfunction underlies or contributes to many diseases and disorders including cancer (see O'Rourke, 2000, J. Physiol., 529:23-36; Zhao et al., 2012, Oncogene: doi:10.1038/one.2012.1494; and U.S. Provisional Patent Application No. 61/696,631), metabolic disease (see Herlein et al., 2010, Metabolism 59:247-257; and Jelenik & Roden, 2012, Antioxidants & Redox Signaling: doi:10.1089/ars.2012.4910), neurodegenerative diseases (see Johri & Beal, 2012, J. Pharma and Exper. Thera. 342: 619-630), and aging (see Wallace et al., 2010, Ann. Rev. Path.: Mech. of Disease, 5:297-348). To the best of the current inventors' knowledge, there are no known therapeutic treatments for mitochondria-based, CaMKII-associated diseases and disorders

SUMMARY

The present inventors have determined that CaMKII is present in mitochondria and further that CaMKII may stimulate mitochondrial calcium uniporter (MCU) activity. Further to this determination, cationic biodegradable nanoparticles that are targeted to mitochondria and that comprise CaMKII inhibitors may be administered in methods for treating or preventing diseases and disorders associated with mitochondrial CaMKII activity and subsequent MCU activity. Methods of treating and preventing diseases and disorders associated with mitochondrial CaMKII activity are proposed whereby MCU activity is modulated by CaMKII inhibitors in order to achieve a therapeutic or preventive effect.

The disclosed cationic biodegradable nanoparticles include a CaMKII inhibitor agent and a mitochondrial location sequence (MLS) peptide to facilitate specific targeting of the nanoparticles to mitochondria.

In some embodiments, the disclosed cationic biodegradable nanoparticles include or are formed from dendrimers (e.g., polyamidoamine (PAMAM) dendrimers). The disclosed cationic biodegradable nanoparticles also typically include or are formed from a biodegradable polymer (e.g., polylactic-co-glycolic acid (PLGA)). In some embodiments, the nanoparticles include or are formed from a cationic surfactant (e.g., quaternary ammonium compounds such as cetyltrimethylammonium bromide (CTAB)).

Preferably, the disclosed cationic biodegradable nanoparticles have physical properties that facilitate uptake by a targeted cell and further facilitate uptake by a mitochondria. These physical characteristics may include, but are not limited to, a mean average diameter between about 25 nm and about 500 nm and a positive zeta-potential between about 5 mV and about 45 mV.

The disclosed cationic biodegradable nanoparticles typically include a CaMKII inhibitor. In some embodiments, the CaMKII inhibitor is a peptide (e.g., KRPPKLGQIGRAKRV-VIEDDR (SEQ ID NO:1)). In other embodiments, the CaMKII inhibitor is KN-93 or an analog or derivative thereof that inhibits CaMKII. In further embodiments, the CaMKII inhibitor is an aryl-indolyl maleimide. Preferably, the CaMKII inhibitor inhibits phosphorylation of the mitochondrial calcium uniporter (MCU) by CaMKII at serine residue 57 and/or at serine residue 92

The presently disclosed cationic biodegradable nanoparticles may be formulated as pharmaceutical compositions. Accordingly, also disclosed are method of treating a disease or disorder associated with mitochondrial CaMKII activity in a patient in need thereof, the method comprising administering a CaMKII inhibitor agent targeted to mitochondria (e.g., a pharmaceutical composition comprising the presently disclosed cationic biodegradable nanoparticles).

Suitable diseases and disorders treated and/or prevented by the disclosed methods may include heart disease, disorders, and symptoms thereof. In some embodiments, the disclosed methods may reduce myocardial death and dysfunction after an episode of ischemic heart disease. In particular, the disclosed methods may include treating heart disease, disorders, and symptoms thereof by mitochondrial-targeted CaMKII inhibition and subsequent inhibition of phosphorylation of MCU by CaMKII.

Other suitable diseases and disorders treated and/or prevented by the disclosed methods may include cell proliferative diseases or disorders, such as cancers, metabolic disease, neurodegenerative diseases (e.g., Alzheimer's disease), and aging. In particular, the disclosed methods may include treating these diseases and disorders by mitochondrial-targeted CaMKII inhibition and subsequent inhibition of phosphorylation of MCU by CaMKII.

BRIEF DESCRIPTION OF THE DRAWINGS

FIG. 1 provides the amino acid sequences of an exemplary mitochondrial localization sequence (MLS) from Cox8a protein and of a peptide inhibitor of CaMKII.

DETAILED DESCRIPTION

Figure 2:
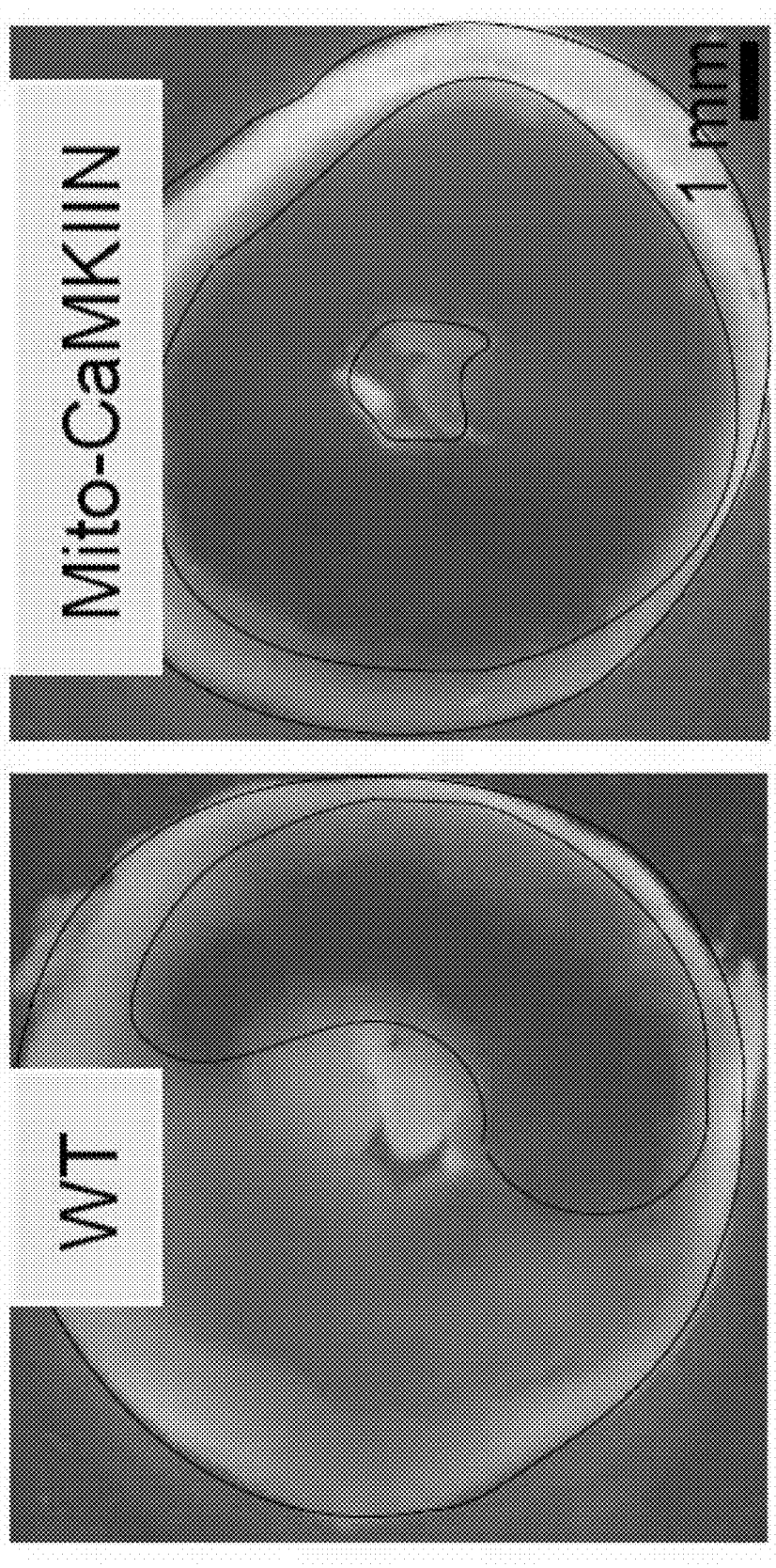
FIG. 2 illustrates that mitoCaMKIIN hearts are resistant to I/R injury. Heart slices were stained with 2,3,5-triphenyltetrazolium chloride (TTC), a marker of cell viability. Pale and white areas indicate dead tissue. Hearts were sectioned after disruption of blood flow to the heart. The heart expressing mitoCaMKIIN shows resistance to I/R injury as it retains about twice the amount of viable tissue.

The disclosed subject matter further may be described utilizing terms as defined below.

Unless otherwise specified or indicated by context, the terms "a", "an", and "the" mean "one or more." For example, an "inhibitor" should be interpreted to mean "one or more inhibitors."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" may be used interchangeably with the terms "comprise" and "comprising."

As used herein, the term "patient" may be used interchangeably with the term "subject" or "individual" and may include an "animal" and in particular a "mammal." Mammalian subjects may include humans and other primates, domestic animals, farm animals, and companion animals such as dogs, cats, guinea pigs, rabbits, rats, mice, horses, cattle, cows, and the like.

A "patient in need thereof" is intended to include a patient having or at risk for developing diseases and disorders associated with CaMKII activity. In particular, a "patient in need thereof" is intended to include a patient having or at risk for developing diseases and disorders associated with mitochondrial CaMKII activity.

A "patient in need thereof" is intended to include a patient having or at risk for developing diseases and disorders associated with heart disease, such as coronary heart disease and the symptoms thereof. Such diseases may include ischemic heart disease, congestive heart failure, heart attacks, strokes, arrhythmias, and heart valve problems. In some embodiments, the disclosed pharmaceutical compositions are administered to treat or prevent myocardial death and/or dysfunction after a myocardial infarction. By "myocardial infarction" is meant an ischemic injury to the heart in which part of the myocardium (heart muscle) has undergone necrosis or apoptosis (i.e., programmed cell death). An "ischemic injury" means the damage or potential damage to an organ or tissue that results from the interruption of blood flow to the organ or tissue (i.e., an ischemic event).

A "patient in need thereof" also may include a patient having, suspected of having, or at risk for acquiring hyperplasia or cancer (e.g., breast cancer, leukemia, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, prostate cancer, liver cancer (e.g., hepatocellular carcinoma), kidney cancer (e.g., renal cell carcinoma), cervical cancer, Kaposi's sarcoma and ovarian cancer. A "patient in need thereof" also may include a patient having, suspected of having, or at risk for acquiring a metabolic disease or disorder (e.g., diabetes). A "patient in need thereof" also may include a patient having, suspected of having, or at risk for acquiring a neurodegenerative disease or disorder (e.g., Alzheimer's disease).

As used herein, the phrase "therapeutically effective amount" shall mean that drug dosage that provides the specific pharmacological response for which a therapeutic agent is administered in a significant number of subjects in need of such treatment. A therapeutically effective amount of a therapeutic agent that is administered to a particular subject in a particular instance will not always be effective in treating the conditions/diseases described herein, even though such dosage is deemed to be a therapeutically effective amount by those of skill in the art.

As used herein, the terms "treatment," "treat," or "treating" refer to therapy or prophylaxis of diseases, disorders, and the symptoms thereof in a subject in need thereof. Therapy or prophylaxis typically results in beneficial or desirable clinical effects, such as alleviation of symptoms, diminishment of extent of disease, stabilization (i.e., not worsening) of the state of the disease, delay or slowing of disease progression, amelioration or palliation of the disease state, and remission (whether partial or total and, whether detectable or undetectable). "Treatment" can also mean prolonging survival as compared to expected survival if a patient were not to receive treatment. Those in need of treatment include those already with the condition or disorder as well as those prone to have the condition or disorder or those in which the condition or disorder is to be prevented.

The methods disclosed herein may include methods of modulating CaMKII activity and/or MCU activity. As used herein, "modulating" means "changing" or "regulating" and may include "inhibiting" CaMKII activity and/or MCU activity.

Disclosed herein for use in the afore-mentioned methods are cationic biodegradable nanoparticles that include an inhibitor of CaMII activity and that are targeted to mitochondrial via including a mitochondrial localizing sequence (MLS). Biodegradable nanoparticles have been described in the art. (See, e.g. Reis et al., Nanomedicine 2 (I) (2006) 8-21; and Kumari et al., Colloids and Surfaces B: Biointerfaces 75 (2010) 1-18; the contents of which are incorporated herein by reference in their entireties).

The disclosed cationic biodegradable nanoparticles may include or may be formed from biodegradable polymeric molecules, which in some embodiments may include dendrimers. Suitable dendrimers may include, but are not limited to, polyamidoamine (PAMAM) dendrimers. Polyamidoamine dendrimers have been used in the art as vehicles for intracellular delivery of therapeutics. (See Esfand et al., Drug Discov. Today (2001) 6(8):427-436; and Bharali, International Journal of Nanomedicine (2009) 4:1-7; the contents of which are incorporated herein by reference in their entireties). Polyamidoamine dendrimers suitable for preparing the presently disclosed nanoparticles may include 3rd-, 4th-, 5th-, or preferably at least 6th-generation dendrimers.

The disclosed cationic biodegradable nanoparticles may include or may be formed from other biodegradable polymeric molecules which may include, but are not limited to polylactic acid (PLA), polyglycolic acid (PGA), co-polymers of PLA and PGA (i.e., polyactic-co-glycolic acid (PLGA)), poly-ε-caprolactone (PCL), polyethylene glycol (PEG), poly (3-hydroxybutyrate), poly(p-dioxanone), polypropylene fumarate, poly(orthoesters), polyol/diketene acetals addition polymers, poly-alkyl-cyano-acrylates (PAC), poly(sebacic anhydride) (PSA), poly(carboxybiscarboxyphenoxyphenoxy hexone (PCPP) poly[bis (p-carboxypheonoxy)methane] (PCPM), copolymers of PSA, PCPP and PCPM, poly(amino acids), poly(pseudo amino acids), polyphosphazenes, derivatives of poly[(dichloro)phosphazenes] and poly[(organo) phosphazenes], poly-hydroxybutyric acid, or S-caproic acid, elastin, gelatin, and chitosan. (See, e.g., Kumari et al., Colloids and Surfaces B: Biointerfaces 75 (2010) 1-18; and U.S. Pat. Nos. 6,913,767; 6,884,435; 6,565,777; 6,534,092; 6,528, 087; 6,379,704; 6,309,569; 6,264,987; 6,210,707; 6,090,925; 6,022,564; 5,981,719; 5,871,747; 5,723,269; 5,603,960; and 5,578,709; and U.S. Published Application No. 2007/ 0081972; and International Application Publication Nos. WO 2012/115806; and WO 2012/054425; the contents of which are incorporated herein by reference in their entireties). In some embodiments, the nanoparticles may include a mixture of PLGA and PAMAM. For example, suitable ratios of PLGA:PAMAM used for preparing the nanoparticles may include ratios such as (6-2): 1, (5-3): 1, and 4:1.

The nanoparticles may include a surfactant which may include a cationic surfactant. Suitable cationic surfactants may include but are not limited to quaternary ammonium compounds, for example, quaternary ammonium compounds or salts thereof having a formula $(X)_3N^+(CH_2)_n(CH_3)$ where X is $C_{1-6}$ alkyl or aryl, and n=(9, 11, 13, 15, or 17). Suitable salts of the quaternary ammonium compounds may include halide salts (e.g., Cl⁻ or Br⁻ salts) such as cetyltrimethylammonium bromide (CTAB).

The disclosed cationic biodegradable nanoparticles may be prepared by methods known in the art. (See, e.g., Nagavarma et al., Asian J. of Pharma. And Clin. Res., Vol 5, Suppl 3, 2012, pages 16-23; Cismaru et al., Rev. Roum. Chim., 2010, 55(8), 433-442; and International Application Publication Nos. WO 2012/115806; and WO 2012/054425; the contents of which are incorporated herein by reference in their entireties). Suitable methods for preparing the nanoparticles may include methods that utilize a dispersion of a preformed polymer, which may include but are not limited to solvent evaporation, nanoprecipitation, emulsification/solvent diffusion, salting out, dialysis, and supercritical fluid technology. In some embodiments, the nanoparticles may be prepared by forming a double emulsion (e.g., water-in-oil-in-water) and subsequently performing solvent-evaporation. The nanoparticles obtained by the disclosed methods may be subjected to further processing steps such as washing and lyophilization, as desired. Optionally, the nanoparticles may be combined with a preservative (e.g., trehalose).

The disclosed cationic biodegradable nanoparticles preferably have physical properties that facilitate uptake by a targeted cell and further facilitate uptake by a mitochondria. For example, preferably the nanoparticles have a size and a charge that that facilitate uptake by a targeted cell and further facilitate uptake by a mitochondria. Typically, the nanoparticles have a mean effective diameter of less than 1 micron, and preferably the nanoparticles have a mean effective diameter of between about 25 nm and about 500 nm, and more preferably between about 50 nm and about 250 nm, and most preferably about 100 nm to about 150 nm. The size of the particles (e.g., mean effective diameter) may be assessed by known methods in the art, which may include but are not limited to transmission electron microscopy (TEM), scanning electron microscopy (SEM), Atomic Force Microscopy (AFM), Photon Correlation Spectroscopy (PCS), Nanoparticle Surface Area Monitor (NSAM), Condensation Particle Counter (CPC), Differential Mobility Analyzer (DMA), Scanning Mobility Particle Sizer (SMPS), Nanoparticle Tracking Analysis (NTA), X-Ray Diffraction (XRD), Aerosol Time of Flight Mass Spectroscopy (ATFMS), and Aerosol Particle Mass Analyzer (APM).

The disclosed cationic biodegradable nanoparticles preferably have a zeta-potential that facilitates uptake by a target cell and/or localization to mitochondria. Typically, the nanoparticles have a zeta-potential greater than 0. In some embodiments, the nanoparticles have a zeta-potential between about 5 mV to about 45 mV, between about 15 mV to about 35 mV, or between about 20 mV and about 30 mV. Zeta-potential may be experimental determined via characteristics that include electrophoretic mobility or dynamic electrophoretic mobility. Electrokinetic phenomena and electroacoustic phenomena may be utilized to calculate zeta-potential.

Nanoparticles will be taken up by cells non-specifically even if they nanoparticles do not include a specific ligand on their surface. However, the disclosed cationic biodegradable nanoparticles are configured such that they are specifically targeted to mitochondria via a ligand. Typically, the nanoparticles comprise a mitochondrial localization sequence (MLS), which is a peptide that facilitates uptake of the nanoparticle by mitochondria. As such, the MLS typically is present on the surface of the nanoparticle. Mitochondrial localization sequences are known in the art. (See, e.g., Neupert, W. (1997), Annu. Rev. Biochem 66, 863-917; Moir et al., (1998), Biochim. Biophys. Acta 1403, 12-27; Voos et al., (1999), Biochim. Biophys. Acta 1422, 235-254; Pfanner (2000) Curr. Biol. 10 R412-R415; Diekert et al., (1999), Proc. Nat'l. Acad. Sci. USA, 96:11752-11757; and Neve et al., J. Biol. Chem. 2001, 276:11317-11322; the contents of which are incorporated herein by reference in their entireties). In some embodiments, the nanoparticles may include, but are not limited to, a MLS that comprises an amino acid sequence MSVLTPLLLRGLTGSARRLPVPRAKIHSLL (SEQ ID NO:2), which is derived from the mitochondrial protein Cox8a. (See, e.g., Joiner et al., Nature, 2012. 491(7423):p. 269-73; the content of which is incorporated herein by reference in its entirety).

The MLS may be covalently or non-covalently bound to one or more components of the nanoparticle. In some embodiments, the MLS is bound to the surface of the nanoparticles via a biotin/avidin linkage. For example, biotin may be conjugated to the nanoparticles using ethyl(dimethylaminopropyl)carbodiimide/N-Hydroxysuccinimide (EDC/NHS) chemistry (see U.S. Published Application Nos. U.S. 2007/0259382; and U.S. 2010/0190257; the contents of which are incorporated by reference in their entireties). Biotinylated MLS ligands may be purchase from a commercial source (e.g., AnaSpec, Fremont, Calif.). The MLS ligand then may be bound to the surface of the nanoparticles using the avidin-biotin binding interaction using methods previously described. (See, e.g., Sakhalkar et al., Proc. Nat'l Acad. Sci. USA, 2003 100(26): p. 15985-15900; Salem et al., Biomacromolecules, 2001. 2(2): p. 575-580; Salem et al., Adv. Mater., 2003. 15(3): p. 201; Salem et al., Adv. Mater. 16(3): p. 268; and Krishnamachari et al., Adv. Mater., 2008. 20(5): p. 989; the contents of which are incorporated herein by reference in their entireties). In other embodiments, MLS ligands may be conjugated to the surface of nanoparticles via their carboxy-terminus using EDC/NHS chemistry using methods previously described. (See, e.g., Zhang et al., Bioconjugate Chemistry. 2007. 18(6): p. 2068-2076; Hong et al., Tissue Engineering Part C-Methods, 2011. 17(3): p. 319-325; Zhang et al., J. Microencapsulation, 2008. 25(1): p. 1-12; and Sinclair et al., Biomaterials, 2006. 27(9): p. 2090-4; the contents of which are incorporated herein by reference in their entireties). In another embodiment, the MLS ligands may be adsorbed to the surface of the nanoparticles using methods previously described. (See, e.g., Lemke et al., Biomaterials, 2013. 34(10): p. 2524-9; and Singh et al., Curr. Drug Deliv. 2006. 3(1):11-220; the contents of which are incorporated herein by reference in their entireties).

The disclosed cationic biodegradable nanoparticles include a CaMKII inhibitor, which are known in the art. (See, e.g., U.S. Pat. No. 7,320,959, and U.S. Pat. No. 8,440,656; the contents of which are incorporated herein by reference in their entireties, particularly the patent disclosure related to CaMKII inhibitors). In some embodiments the CaMKII inhibitor may be peptide, which may include but is not limited to, a peptide comprising an amino acid sequence of the alpha form of the endogenous inhibitor of CaMKII called CamKIIN. (See, e.g. Chang et al., PNAS USA 1998 95(18): 10890-5; and Illario et al., J. Biol. Chem. 2003 278(46): 45101-8; the contents of which are incorporated herein by reference in their entireties). For example, the peptide inhibitor of CaMKII may comprise the amino acid sequence KRPPKLGQIGRAKRVVIEDDR (SEQ ID NO:1) otherwise referred to as "CaMKIINtide." Other peptide inhibitors are known in the art (See, e.g., Chao et al., Nat. Struct. Mol. Biol., 2010, 17(3): 264-72; and Ashpole et al., J. Biol. Chem. 2012 287(11):8495-8506; the contents of which are incorporated herein by reference their entireties).

CaMKII inhibitors may include aryl-indolyl maleimide compounds. (See, e.g., Levy et al., "Aryl-indolyl maleimides as inhibitors of CaMKIIδ. Part 1: SAR of the aryl region," Biorg. & Medic. Chem. Lett 18 (2008) 2390-2394; Levy et al., "Aryl-indolyl maleimides as inhibitors of CaMKIIδ. Part 2: SAR of the amine tether," Biorg. & Medic. Chem. Lett 18 (2008) 2395-2398; and Lu et al., "Aryl-indolyl maleimides as inhibitors of CaMKIIδ. Part 3: Importance of the indole orientation," Biorg. & Medic. Chem. Lett 18 (2008) 2399-2403; the contents of which are incorporated by reference in their entireties).

CaMKII inhibitors may include the compound known as KN-93 or related compounds, analogs, or derivatives thereof having CaMKII inhibitory activity. Referring to the PubChem Database provided by the National Center for Biotechnology Information (NCBI) of the National Institute of Health (NIH) at its website, CaMKII inhibitors contemplated herein may include the compounds referenced by compound identification (CID) Nos. 5312122, 16760530, 6419757, which entries are incorporated herein by reference in their entireties. Compounds related to KN-93, analogs, or derivatives thereof may include, for example, compounds referenced by compound identification (CID) Nos. 3837, 6419758, 18412788, 16760530, 9983993, 5353702, 3836, 24906277, 16219540, and 8122359, which entries are incorporated herein by reference in their entireties.

The disclosed cationic biodegradable nanoparticles may be formulated together with one or more suitable carriers, diluents, or excipients as part of a pharmaceutical composition for treating or preventing a disease or disorder associated with mitochondrial CaMKII activity in a patient in need thereof. The term "pharmaceutical composition" may be utilized herein interchangeably with the term "therapeutic formulation." Therapeutic formulations of the cationic biodegradable nanoparticles used in accordance with the present methods may be prepared for storage by mixing the cationic biodegradable nanoparticles having a desired degree of purity with optional pharmaceutically acceptable carriers, excipients or stabilizers (Remington's Pharmaceutical Sciences 16th edition, Osol, A. Ed. (1980)), for example in the form of lyophilized formulations or aqueous solutions. In addition to the pharmacologically active compounds such as the nanoparticles, the compositions used in the therapeutic methods disclosed herein may contain one or more suitable pharmaceutically acceptable carriers comprising excipients and auxiliaries that facilitate processing of the active compounds into preparations that can be used pharmaceutically.

The disclosed cationic biodegradable nanoparticles may be administered together with a pharmaceutically acceptable carrier. A "pharmaceutically acceptable" carrier typically is not biologically or otherwise undesirable, i.e., the carrier may be administered to a subject, along with the cationic biodegradable nanoparticles without causing any undesirable biological effects or interacting in a deleterious manner with the cationic biodegradable nanoparticles or any of the other components of the pharmaceutical composition in which the cationic biodegradable nanoparticles are contained. In some embodiments, the carrier may be selected to minimize any degradation of the cationic biodegradable nanoparticles or any of the other components of the pharmaceutical composition or to minimize any adverse side effects in the subject in need thereof.

The disclosed cationic biodegradable nanoparticles may be administered in any suitable manner. However, in some embodiments, the cationic biodegradable nanoparticles are present in a pharmaceutical composition that is administered via injection (e.g., intravenous injection, peritoneal injection, or subcutaneous injection). For example, the nanoparticles may be combined with pharmaceutically acceptable carriers, diluents, or excipients that are suitable for injection such as saline, Ringer's solution, dextrose solution, and the like. The particular dosage regimen, i.e., dose, timing and repetition, will depend on the particular individual and that individual's medical history. Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 µg/kg body weight, at least about 100 µg/kg body weight; at least about 50 µg/kg body weight; at least about 10 µg/kg body weight; at least about 1 µg/kg body weight, or less, is administered.

The pharmaceutical preparations utilized in the methods disclosed herein may be manufactured by means that include, but are not limited to, mixing, granulating, dissolving, or lyophilizing processes. Thus, for example, pharmaceutical preparations for intravenous use can be obtained by combining the cationic biodegradable nanoparticles with a liquid excipient and preparing a suspension for injection. Aqueous injection suspensions can contain substances such as sodium carboxymethyl cellulose, sorbitol, and/or dextran. Optionally, the suspension may also contain stabilizers.

Formulations to be used for in vivo administration in the disclosed methods typically are sterile. Sterile compositions may be prepared, for example, by filtration through sterile filtration membranes.

The presently disclosed cationic biodegradable nanoparticles may be formulated as a pharmaceutical composition and administered to a patient in need thereof in order to treat or prevent a disease or disorder associated with mitochondrial CaMKII activity. For example, the methods may include treating or preventing heart disease or the symptoms thereof. In some embodiments, the disclosed pharmaceutical compositions are administered to treat or prevent myocardial death and/or dysfunction after a myocardial infarction. By "myocardial infarction" is meant an ischemic injury to the heart in which part of the myocardium (heart muscle) has undergone necrosis or apoptosis (i.e., programmed cell death). An "ischemic injury" means the damage or potential damage to an organ or tissue that results from the interruption of blood flow to the organ or tissue (i.e., an ischemic event).

In other embodiments the presently disclosed cationic biodegradable nanoparticles may be formulated as a pharmaceutical composition and administered to a patient having, suspected of having, or at risk for acquiring hyperplasia or cancer (e.g., breast cancer, leukemia, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, prostate cancer, liver cancer (e.g., hepatocellular carcinoma), kidney cancer (e.g., renal cell carcinoma), cervical cancer, Kaposi's sarcoma and ovarian cancer.

EXAMPLES

The following examples are illustrative and are not intended to limit the disclosed subject matter.

Example 1

Mitochondria Targeted Nanoparticles that Protect Against Myocardial Cell Death

Abstract

Disclosed are methods for preparing engineered nanoparticles composed of polyamidoamine (PAMAM) dendrimers and polylactic-co-glycolic acid (PLGA). The nanoparticles may be taken up by cardiac myocytes, escape from the endosomal/lysosomal pathway, and accumulate in mitochondria where they can specifically deliver a peptide that inhibits CaMKII activity. Conjugation of a mitochondria localization sequence (MLS) to the surface of these nanoparticles may significantly improve the accumulation of the peptide loaded particles in the mitochondria.

Background

Ischemic heart disease is a major cause of morbidity and death in the western world [1]. Mitochondria dysfunction plays a key role in the pathogenesis of ischemia and cardiomyopathy [1]. However, few mitochondria targeting drugs have been successfully developed and these types of drug candidates and their effective delivery remains a critical need [1]. We and others have reported that over-activation of the $Ca^{2+}$ and calmodulin-dependent protein kinase II (CaMKII) by $Ca^{2+}$ triggers myocardial death and heart failure [2-4]. CaMKII over-activation creates multiple defects in myocardial $Ca^{2+}$ homeostasis, including increased mitochondrial $Ca^{2+}$ [4-6]. CaMKII inhibition is protective against I/R, MI and neurohumoral toxicity, clinically relevant forms of myocardial injury marked by disturbed intracellular $Ca^{2+}$ homeostasis [2-4, 7].

Excessive increases in mitochondrial $Ca^{2+}$ lead to mitochondrial permeability transition pore (mPTP) opening and dissipation of the mitochondrial inner membrane potential ($\Delta\Psi m$) [4, 8, 9]. CaMKII catalytic activity was identified to be the mechanism for $Ca^{2+}$ to affect downstream responses to I/R injury, through the testing of mice with myocardial-delimited CaMKII inhibition that were developed by transgenic expression of a membrane-targeted CaMKII inhibitor, CaMKIIN, the most potent and specific CaMKII inhibitory protein [4, 10], endogenous to brain. To determine if mitochondrial-targeted CaMKIIN (mitoCaMKIIN) transgenic mice were resistant to I/R injury by a $Ca^{2+}$-regulated pathway we used isolated, perfused, working mouse hearts to directly measure myocardial mechanical responses to I/R injury under conditions designed to restrict glycolytic metabolism. Left ventricular developed pressure and the first derivative of left ventricular developed pressure were reduced in wild-type (WT) vehicle-treated hearts after I/R injury, but were preserved after I/R injury in hearts with mitochondrial CaMKII inhibition. The area of infarcted myocardium following I/R injury was 66±3.3 percent of the area at risk for WT hearts and was reduced by half with mitochondrial CaMKIIN expression (FIG. 2) [4]. The relative area of infarcted myocardium was inversely related to the extent of mechanical recovery, suggesting that the beneficial effects of CaMKII inhibition ultimately derived from prevention of myocardial death in response to I/R injury. Caspase 9, a marker of mitochondrial-triggered apoptosis [11] was significantly reduced in the mitoCaMKIIN transgenic hearts after I/R injury. We have shown that mitochondrial-restricted expression of CaMKIIN protects mitochondria from I/R injury.

Mitochondria are structurally dynamic organelles and loss of the highly ordered internal membrane cristae is an ultrastructural correlate of mPTP opening, loss of $\Delta\Psi m$ and apoptosis initiation [12]. We used transmission electron microscopy to examine mitochondrial ultrastructure and to quantify mitochondrial disruption after I/R injury. Mitochondria of vehicle-treated WT hearts suffered extensive disruption after I/R injury. In contrast, mitochondria from CaMKIIN transgenic hearts were resistant to I/R injury [4]. Our previous studies have shown that infarct size, mitochondrial structural integrity, mitochondrial-triggered cell death and dysfunction are improved by CaMKII inhibition, consistent with a concept where CaMKII activation engages a mitochondrial pathway leading to mPTP opening during pathological stress [4]. Development of a therapeutic strategy to prevent mitochondria triggered cell death linked to overactivation of CaMKII requires the identification of a target peptide sequence that can inhibit CaMKII and the development of a targeted drug delivery strategy that is capable of entering cells, escaping the endosomal/lysosomal compartments and delivering the peptide sequence to the mitochondria.

Figure 3:
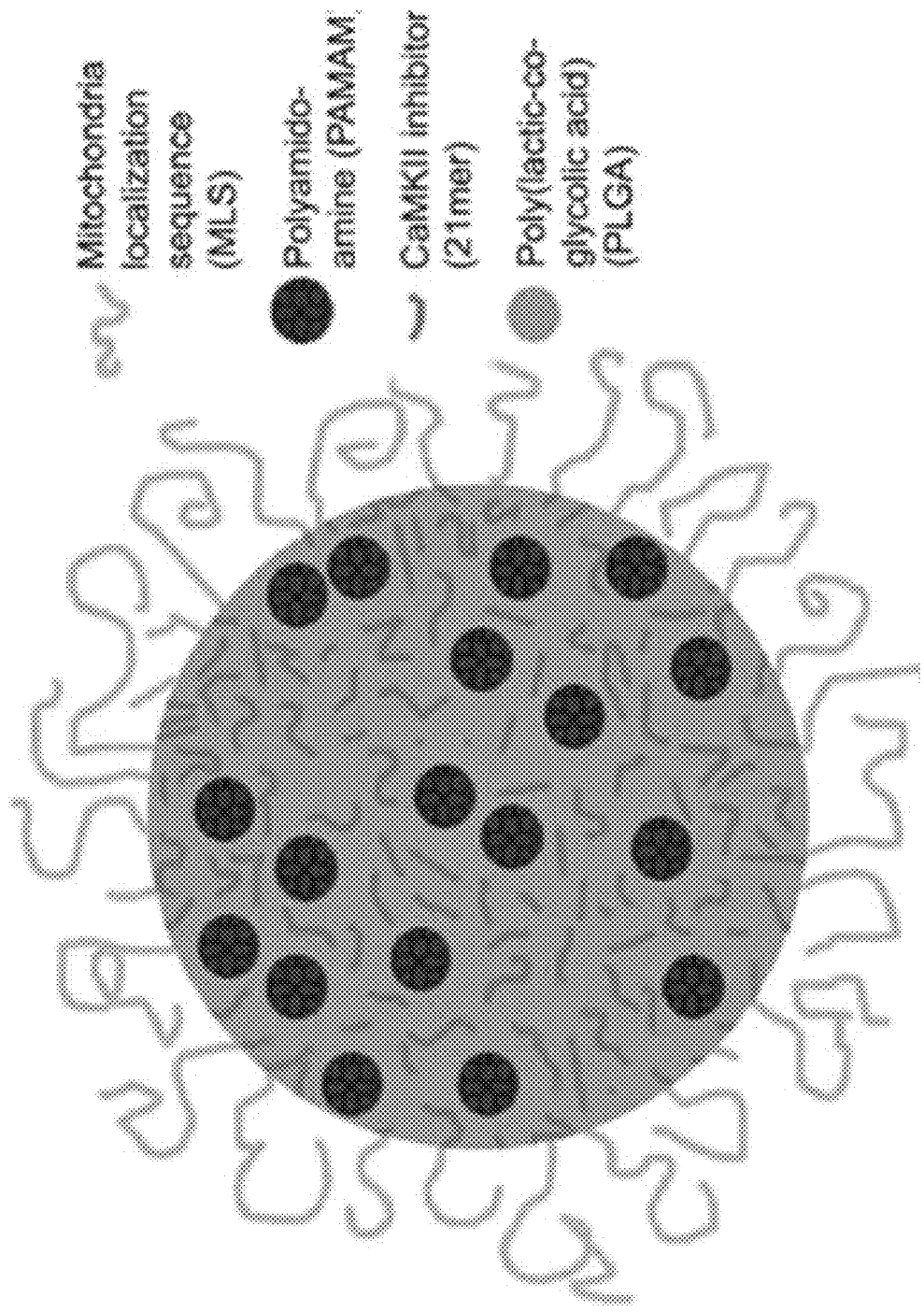
FIG. 3 provides a schematic representation of a mitochondrial-targeted peptide-loaded PLGA/PAMAM nanoparticle delivery system.

Recently, a peptide sequence was reported with similarity to the regulatory domain of CaMKII that inhibits CaMKII substrate phosphorylation with an IC50 of 0.12 M [13]. Here, we propose an innovative nanoparticle delivery system that is composed of polyamidoamine (PAMAM) dendrimers and polylactic-co-glycolic acid (PLGA) and can efficiently be taken up by cardiac myocytes, escape from the endosomal/lysosomal pathway, and target the mitochondria where they can specifically deliver peptides that inhibit CaMKII (FIG. 3). To the best of the inventors' knowledge, this is the first study to propose conjugating mitochondria localization sequences (MLS, FIG. 1) to the surface of nanoparticles for targeted peptide delivery to the mitochondria, and no study to date has developed a targeted biodegradable polymer nanoparticle based delivery system for specific inhibition of CaMKII in mitochondria. Our proposed nanoparticle therapy may be evaluated for protection against ischaemia reperfusion, myocardial infarction and neurohumoral toxicity in wild-type and transgenic CaMKII mouse models [4]. In addition, the innovative platform delivery system we develop has potential for treatment of a wide variety of other disorders based on mitochondrial dysfunction including cancer and Alzheimer's disease.

Research Design and Methods

Development and Characterization of PLGA/PAMAM Nanoparticles that are Loaded with CaMKII Inhibitor Peptides and Surface-Conjugated with MLS Ligands and Monitoring of Intracellular Trafficking of Nanoparticles to the Mitochondria in H9C2 Cells and Primary Neonatal Heart Cells.

These studies will identify the optimum size, surface charge and MLS surface ligand density for optimal delivery of the peptide inhibitors to mitochondria. We propose that cationic nanoparticles containing PAMAM dendrimers will bind effectively to the cell surface, which will promote endocytic uptake, will be buffered against the endosomal compartments, and will be released into the cytoplasm. The nanoparticle then will be localized to the mitochondria via MLS targeting. We propose that nanoparticles loaded with peptide inhibitors at 40-50% loading efficiency that are in the 100 nm size range and that have positive (circa 20-30 mV) zeta-potentials and that are surface engineered with medium to high density MLS ligands will be the most efficient formulation for mitochondrial delivery of peptide inhibitors.

Figure 4:
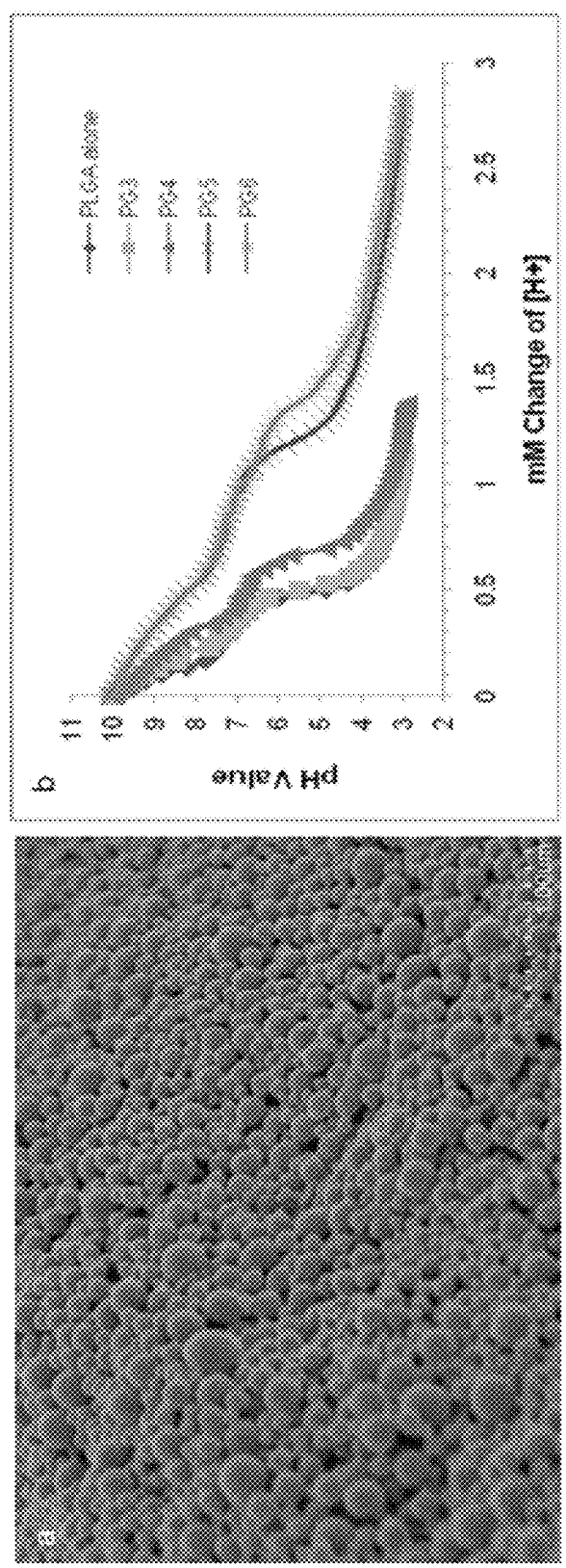
FIG. 4. a) Scanning electron microscopy (SEM) images show that PLGA/PAMAM nanoparticles are smooth and spherical in appearance. b) Acid titration experiments with 0.1 N HCl illustrate the buffering capacity of PLGA/PAMAM particles versus PLGA particles. The PG number denotes the generation of the PAMAM dendrimer used to prepare the particle. Particles prepared with higher generation dendrimers illustrated greater buffering capacity.

We will prepare peptide loaded PLGA/PAMAM nanoparticles that are surface conjugated with MLS ligands [14] ranging from 1:1 to 10:1 PLGA:PAMAM ratios by mass. We will test PAMAM dendrimers that range from generation 3 to generation 6 [15, 16]. We will load the peptide inhibitor into the PLGA/PAMAM polymer mixtures using the water in oil in water double emulsion solvent evaporation methodology and/or the solvent diffusion/nanoprecipitation methodology [15, 17-24]. The peptide has an IC50 of 100 nM, which we will use as a starting point for a dose response curve. Our goal will be to prepare peptide-loaded PLGA/PAMAM nanoparticles that range in size from 80 nm to 500 nm. Pilot studies have shown that cationic PLGA/PAMAM nanoparticles prepared using the double emulsion solvent evaporation method are smooth and spherical in appearance and have relatively narrow polydispersity that may be further improved using differential centrifugation (FIG. 4).

Figure 5:
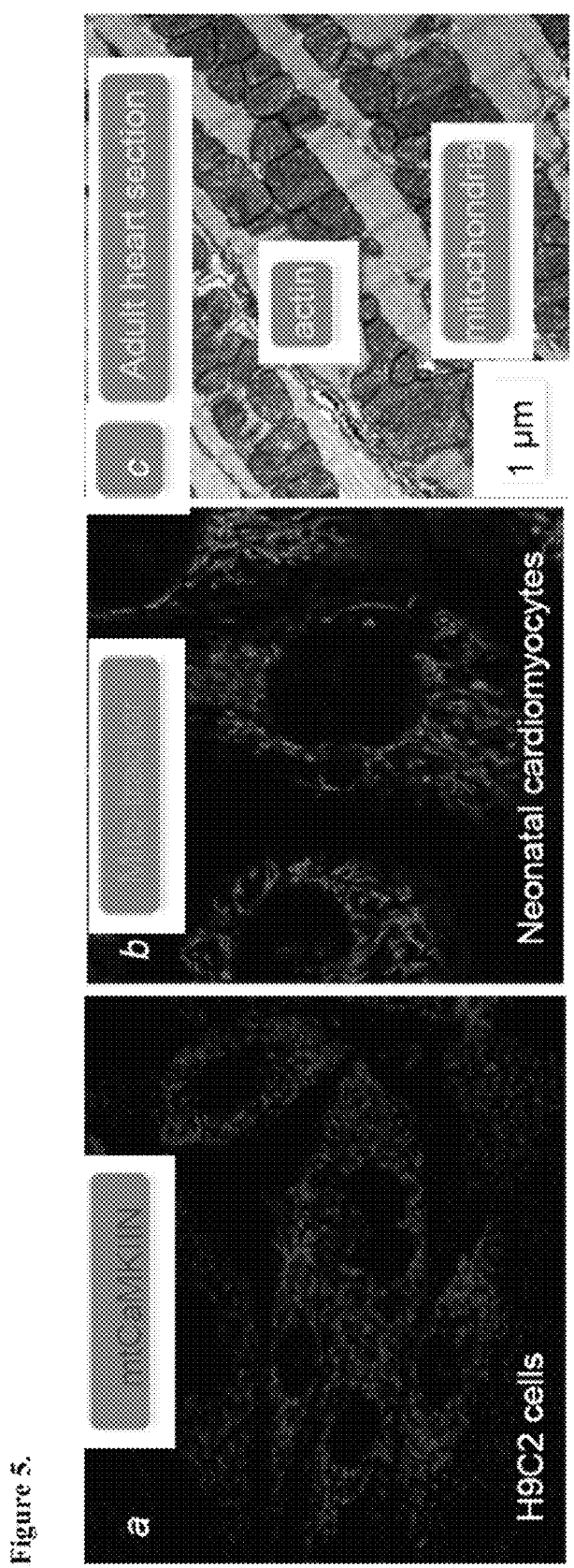
FIG. 5 displays mitochondria from different cell lines and heart tissue. a) H9C2 cells expressing an HA-tagged CaMKII inhibitor. b) Isolated mouse neonatal cells having mitochondria labeled with mitotracker green. c) Electron micrograph of adult heart section showing that mitochondria are on average 2 microns in diameter.

Next, we will conjugate MLS ligands to the surface of the PLGA/PAMAM nanoparticles. The MLS ligand that we will be using is derived from the N-terminus of the matrix mitochondrial protein Cox8a [4]. FIG. 5 shows that GFP tagged MLS ligands can efficiently accumulate in the mitochondria of cardiac cells. MLS-PLGA/PAMAM conjugation will be achieved using three different approaches. In the first approach, we will conjugate biotin to the PLGA/PAMAM nanoparticles using ethyl(dimethylaminopropyl) carbodiimide/N-Hydroxysuccinimide (EDC/NHS) chemistry and purchase biotinylated MLS ligands from AnaSpec (Fremont, Calif.). The MLS ligand will then be bound to the surface of the PLGA/PAMAM nanoparticles using the avidin-biotin binding interaction using methods we have described previously [17, 25-28]. In the second approach, we will conjugate carboxylic acid terminated MLS ligands to the surface of PLGA/PAMAM nanoparticles using EDC/NHS chemistry using methods we have described previously [15, 16, 20, 29]. In the third approach, we will absorb the MLS ligands to the surface of the PLGA/PAMAM nanoparticles using methods we have described previously [30]. We then will characterize loading and release of fluorescein conjugated peptide from the PLGA/PAMAM nanoparticles with and without MLS ligand conjugation using UV-Vis spectroscopy [31]. Rhodamine loaded PLGA/PAMAM nanoparticles with and without MLS ligand conjugation will be prepared for cellular trafficking studies [32, 33]. We will prepare control groups that include PLGA nanoparticles (without PAMAM) with and without MLS ligands, liposomes with and without triphenylphosphonium (TPP), and PLGA nanoparticles with TPP [34-36]. TPP is an alternative mitochondria-targeting molecule that has shown significant potential for enhancing mitochondria delivery using liposomes, cationic polymers and biodegradable nanoparticles [36-39]. Control groups will be prepared with rhodamine-loading or peptide-loading. The size and surface charge of the peptide-loaded PLGA/PAMAM nanoparticles with and without MLS ligand conjugation and all control groups will be measured using the Zeta-sizer Nano ZS. The buffering capacity of the PLGA/PAMAM nanoparticles with and without MLS ligand conjugation and all control groups will be characterized as described previously [20] to correlate to subsequent studies evaluating co-localization with endosomal/lysosomal compartments. Our studies preparing PLGA/PAMAM nanoparticles show that the higher the PAMAM dendrimer generation used to prepare the nanoparticles, the higher the buffering capacity (FIG. 4).

H9C2 cells, a permanent cell line derived from rat cardiac tissue [40] will be grown in differentiating media (DMEM, 2 mM Glutamine, 1% FBS, 10 nM Retinoic Acid). Neonatal cardiomyocytes (1-3 days post natal) will be prepared by dissecting mouse neonatal hearts and incubating with F-10 nutrient medium, containing 140 μg/ml of collagenase type-2 (Sigma) and 440 μg/ml pancreatin (Sigma) until cells are dissociated. The cells will then be washed, resuspended in 1:1 mix of Dulbecco's minimal Eagle's medium (DMEM) and F10 nutrient mix with 5% each of equine and bovine calf serum. These cells will be pre-plated in tissue culture dishes for 1 h to allow for attachment of non-myocytes. The resulting non-adherent myocytes will be plated on fibronectin-coated (Sigma) tissue culture dishes and grown in a 1:1 mix of DMEM and F10 nutrient medium containing 1 μg/ml thyroxin, 5 μg/ml of transferrin, 1 μg/ml of insulin, 10 pM each of LiCl and selenite. A 0.1 mM bromodeoxyuridine concentration will be used to check fibroblast growth [10]. We will evaluate cellular uptake of rhodamine labeled nanoparticles with and without MLS ligands in H9C2 cells and primary neonatal heart cells using confocal microscopy and flow cytometry as described previously [20, 24, 32, 33]. Co-localization of the rhodamine labeled nanoparticles with mitochondria of cells will be achieved by labeling cells with Mitotracker Green (FIG. 5 and Invitrogen) [4].

Evaluation of the rhodamine loaded nanoparticles ability to escape the endosomal and lysosomal compartments will be evaluated by staining cells with Lysotracker Green (Invitrogen) [15]. For both, lysosomal staining and mitochondria staining experiments, we will analyze the images using the ImageJ colocalization finder plugin. We will also carry out experiments in which we stain cells using the early endosomal marker EAA-1, [36, 41]. The ability of nanoparticles to escape from the endosomal/lysosomal compartments will be correlated with buffering capacity measurements to determine if escape from these compartments is due to the proton sponge mechanism. Because the proposed nanoparticles have a net positive charge, they are potentially susceptible to aggregation in serum containing media [42]. To evaluate this, we will incubate nanoparticles with and without MLS ligands in 10% serum containing media and characterize changes in the overall size distribution and average surface charge. Immunogenicity of all nanoparticle based delivery systems should be monitored for therapeutic non-vaccine applications. We will evaluate the immunogenicity of the PLGA/PAMAM nanoparticles with and without MLS ligand conjugation and the control nanoparticles by incubating them in DC2.4 cells which are a pure dendritic cell line that are known to express MHC class I and II and can be stimulated to secret pro-inflammatory cytokines [18]. We will specifically seek to identify secretion of pro-inflammatory cytokines INF-gamma, TNF-alpha and IL-6. All results will be compared to the positive control of incubation of DC2.4 cells with CpG 1826 that is known to up-regulate all three of these pro-inflammatory cytokines [24, 43]. To determine the relative proportions of rhodamine labeled nanoparticles entering the mitochondria of the cells, we will carry out mitochondria separation using sub-cellular isolation experiments as we have described previously [4]. Briefly, isolation of mitochondria will be carried out on ice. The cells will be washed and then homogenized. Nuclei and unbroken cells will be pelleted by centrifugation. The crude mitochondrial and cytosolic fraction will be obtained from the supernatant by centrifugation [4]. The pellet will be further purified and nanoparticle content will be determined by quantified detection of rhodamine using UV-Vis spectroscopy. The proportion of nanoparticles in the cytosol versus the mitochondria will be further verified using TEM. Finally, we will determine the toxicity of the PLGA PAMAM nanoparticles with and without peptide-loading and with and without MLS ligand binding. Toxicity studies will be carried out over a range of concentrations based on the peptide concentration and in separate experiments based on number of particles incubated using the MTS and LDH assays [44]. The mechanism of any cell death observed will be clarified using Annexin V-propodium iodide staining assays [44].

We propose that nanoparticles in the 80-100 nm size range will have the greatest uptake by cells and the greatest accumulation in the mitochondria. The smaller nanoparticles (circa 80 nm) may have loading efficiencies that are 10-15% lower than nanoparticles at the higher end of the size ranges tested (500 nm). Nanoparticles are proposed to provide a burst release of 30-40% of peptide inhibitor within the first 24 hours followed by a more sustained release profile after 24 hours. As the ratio of PAMAM and the generation of the PAMAM increase in the PLGA/PAMAM nanoparticles, we expect to see proportional increases in the buffering capacity and escape from endosomal/lysosomal compartments. The higher content and generation of PAMAM is also expected to lead to higher zeta-potential values/positive surface charges for the PLGA/PAMAM nanoparticles. As the positive surface charge increases, we expect to see proportional increases in the mitochondria accumulation. However the increase in PAMAM content and generation of PAMAM is also expected to increase toxicity such that the optimal nanoparticle construct will be a compromise in buffering capacity and toxicity. We anticipate that a generation 4 PAMAM dendrimer at an 8:2 PLGA:PAMAM ratio could be ideal for our intended application. PLGA/PAMAM nanoparticles will undergo some degree of aggregation in serum containing media but past experience with cationic PLGA particles suggests that it will not be significant [36]. If aggregation is significant, we may utilize PEG spacers between the particles and the MLS ligand to improve the steric stabilization of the nanoparticles [17, 25, 33, 36, 42]. In addition, we expect that the PLGA/PAMAM nanoparticles will trigger some pro-inflammatory cytokines but that these will be negligible relative to the positive controls of CpG 1826. We anticipate that the MLS ligand conjugation to the nanoparticles will maintain a net positive surface charge, incrementally increase the overall size, and significantly increase the proportion of PLGA/PAMAM nanoparticles that accumulate in the mitochondria. The EDC/NHS chemistry has the potential to inactivate the MLS ligand and if this occurs, we will focus on the use of the biotin-avidin interaction that can allow MLS binding under aqueous conditions or we will explore other chemistries, similar to those utilized for proteins such as transferrin [32], peptides such as RGD [45], and ligands such as galactose [21] and mannose [33].

Evaluation of the Effect of Mitochondrial CaMKII Inhibition Induced by the Peptide on Protection Against Ang II Induced Cell Death.

Here, we will characterize CaMKII activity knockdown in H9C2 cells and primary neonatal heart cells following incubation with PLGA/PAMAM nanoparticles loaded with peptide inhibitors with and without surface conjugated MLS ligands. We propose that incubation of peptide-loaded nanoparticles in cells will be significantly more protective than peptides alone against mPTP opening, loss of $\Delta\Psi m$, mitochondrial disruption and programmed cell death in response to incubation with Ang II. Cyclosporin A, which blocks the mitochondrial permeability transition pore, and neonatal cardiomyocytes from mitoCaMKIIN transgenic mouse hearts will be used in control experiments. We propose that surface conjugation of MLS ligands to the nanoparticles will significantly increase the efficacy of the protection generated.

Figure 6:
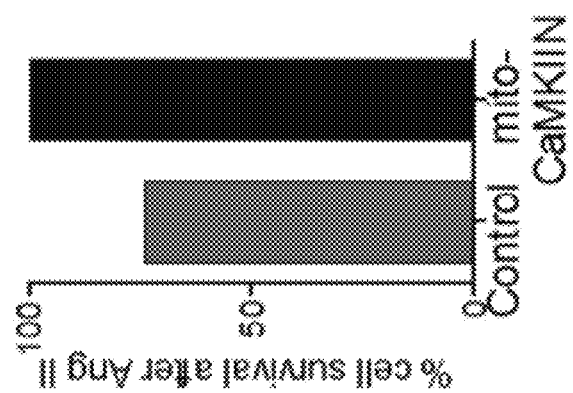
FIG. 6 illustrates that mitoCaMKIIN expression prevents excess mitochondrial ROS generation after treatment with Ang II (1 μM, 3 h). The untransfected H9C2 cell (left) shows increased mitosox fluorescence, which is an indicator of mitochondrial ROS. The graph shows the percent of H9C2 cell survival after Ang II treatment, using ~1,000,000 cells in each group.
Figure 6:
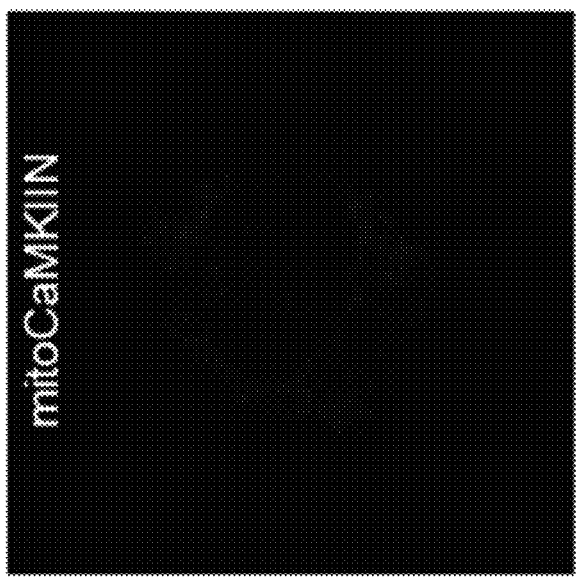
Figure 6:
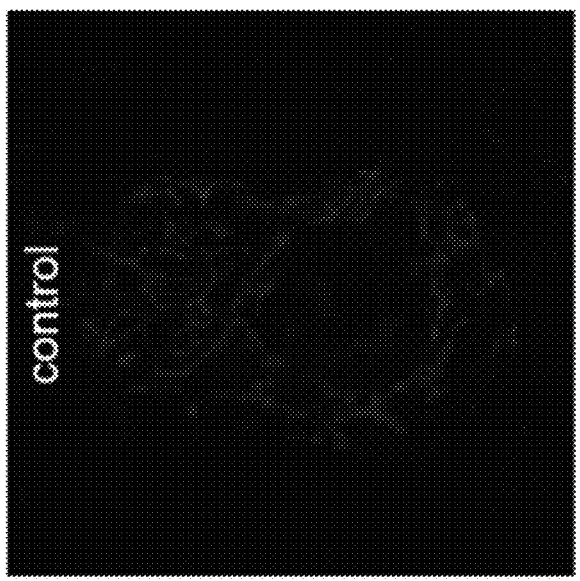

The peptide hormone Ang II induces opening of mitochondrial KATP channels, depolarizes $\Delta\Psi m$, and amplifies ROS generation from mitochondria [46]. We have shown that inhibition of CaMKII can protect against Ang II induced ROS species generation (FIG. 6). H9C2 cells and eventually neonatal cardiomyocytes from WT and mitoCaMKIIN mice will be cultured as described above, and peptide-loaded PLGA/PAMAM nanoparticles with and without surface bound MLS ligands will be prepared as described above. Cells will be treated with Ang II (1 µM for 3 hours). Both H9C2 cells and neonatal cardiomyocytes will be tested. We plan to isolate cardiomyocytes from four mouse litters of mitoCaMKIIN mice. Because these transgenic mice are crossed to WT-C57 mice each generation, the WT littermates will be used to test treated and untreated nanoparticles. A series of increasing doses of nanoparticles will be co-incubated with Ang II to determine the dose-response curve for generating protection against changes induced by Ang II. Nanoparticles will be incubated 2 days before incubation of Ang II, at the same time and 2 days after incubation with Ang II to determine the potential of the nanoparticles to prevent and treat Ang II induced changes in the cells. Control groups will include peptide-loaded into TPP-liposomes [35], Peptide loaded into PLGA-PEG-TPP nanoparticles [39], the full CamKIIN protein both alone and in PLGA/PAMAM nanoparticles, mitoCamKIIN, peptide alone, MLS-peptide, Cyclosporin A (5 µM), and untreated. To characterize the protective effects of peptide-loaded PLGA/PAMAM nanoparticles, we will measure ROS species generation and $Ca^{2+}$-induced injury in isolated mitochondria. Reactive oxygen species production will be estimated by measuring the oxidation of dihydroethidium (DHE, Molecular Probes, Eugene, Oreg.), which becomes fluorescent upon oxidation with superoxide or mitoSOX (FIG. 6, Invitrogen). The Mean Fluorescence Intensity (MFI) data from these experiments will be normalized to levels from H9C2 cells and neonatal cardiomyocytes that are treated with PBS only. The loss of mitochondria function by mPTP opening will be measured in isolated mitochondria in response to supraphysiological increases in mitochondrial $Ca^{2+}$ as we have described previously [4]. Decreases in isolated mitochondrial light scattering at absorbance 450 nm is a correlate of mPTP opening [47]. We will verify our findings with $Ca^{2+}$-induced mitochondria light scattering by a similar assay where a decrease in fluorescence corresponds to a loss of $\Delta\Psi m$. To do this, mitochondria isolated from untreated and nanoparticle treated cells will be processed with a voltage-sensitive tetramethylrhodamine, ethyl ester (TMRE, 10 nM) [12], to test whether peptide inhibition of CaMKII affects $\Delta\Psi m$ responses to $Ca^{2+}$. We will measure mitochondrial $Ca^{2+}$ uptake with a membrane-impermeable indicator, $Ca^{2+}$: Green-5N, [4, 48]. We will determine the overall $Ca^{2+}$ capacity of myocardial mitochondria with serial additions of $Ca^{2+}$. We will measure mitochondrial $Ca^{2+}$ concentration changes in H9C2 cells in response to ATP-evoked $Ca^{2+}$ release using a GFP-based $Ca^{2+}$ indicator, cameleon [49], designed to monitor $Ca^{2+}$ concentration within the mitochondria. Caspase 9 activity assays will be performed on cells treated with Ang II and incubated with and without peptide loaded nanoparticles following manufacturers protocol (Invitrogen) and normalized to protein concentration (tgiml). Transmission electron microscopy studies will be used to evaluate mitochondrial disruption following exposure to Ang II [4]. The degree of protection that incubating peptide-loaded PLGA/PAMAM nanoparticles in H9C2 and neonatal cardiomyocytes provides to mitochondria integrity will be determined using a 4 point system similar to those we have published in the past [4]. Examples of intact mitochondria in cardiac cells can be seen in FIG. 5.

We propose that cells treated with peptide-loaded PLGA/PAMAM nanoparticles will generate significantly lower ROS species than untreated cells when both sets are incubated with Ang II. We also propose that mitochondria from cells that have been incubated with peptide-loaded PLGA/PAMAM nanoparticles will be resistant to $Ca^{2+}$-triggered increases in light scattering compared to mitochondria from untreated cells. We propose that mitochondria isolated from untreated cells will be significantly more sensitive to $\Delta\Psi m$ loss in response to a lethal $Ca^{2+}$ challenge compared to mitochondria from cells that have been treated with peptide-loaded nanoparticles. We propose that cells treated with peptide-loaded nanoparticles will have significantly slower mitochondrial $Ca^{2+}$ uptake, measured as a rate of decrease in $Ca^{2+}$ Green-5N fluorescence, than mitochondria from untreated cells. We propose that peptide-loaded nanoparticle incubation in the cells will increase the mitochondrial $Ca^{2+}$ capacity prior to mPTP opening. We propose that we will observe reduced $Ca^{2+}$ uptake into mitochondria in H9C2 cells as measured by co-expression with mitochondrial-directed cameleon and peptide-loaded PLGA/PAMAM nanoparticles compared with control cells without peptide-loaded PLGA/PAMAM nanoparticle incubation and this will confirm that peptide-loaded PLGA/PAMAM nanoparticles can protect against mitochondrial stress derived from reducing mitochondria $Ca^{2+}$ entry and enhancing mPTP $Ca^{2+}$ tolerance. Cells incubated with peptide-loaded PLGA/PAMAM nanoparticles are proposed to exhibit significantly reduced Caspase 9 activity following treatment with Ang II relative to cells that have not been treated with peptide-loaded nanoparticles. Cells incubated with peptide-loaded PLGA/PAMAM nanoparticles and exposed to Ang II are proposed to provide stronger maintenance of mitochondrial integrity relative to control cells exposed to Ang II. If the differences in mitochondrial integrity are difficult to discern using TEM, we will evaluate the differences in mitochondrial activity by use of the mitochondrial light scattering or $\Delta\Psi m$ with TMRE fluorescent assays. Potentially more potent versions of the peptide can be used if we do not see a significant resistance to Ang II treatment [14]. We propose that the strongest and most significant protection against changes induced by Ang II will be in the cells incubated with peptide-loaded PLGA/PAMAM nanoparticles surface conjugated with MLS ligands relative to all other controls.

Statistical Analysis.

Statistical analysis will be performed using the analysis of variance (ANOVA or Student's t-test, as appropriate). Post hoc pairwise comparisons will be performed using Bonferroni's multiple-comparison test (Prism graph), as appropriate. A p value <0.05 will be considered significant.

Animal Studies.

Future studies will include evaluating our nanoparticle therapy for protection in the whole animal mouse model. Studies will include ischemia reperfusion, myocardial infarction and neurohumoral toxicity in wild-type and two transgenic mouse strains that either overexpress CaMKII or inhibit CaMKII in myocardial mitochondria, as we have previously described in the literature [4] and recently developed. Future studies will also include biodistribution studies of the peptide-loaded PLGA/PAMAM nanoparticles with and without MLS ligands and in vivo dose-response and toxicity studies. The ultimate goal of this research is to develop a platform technology that can realize the potential of mitochondrial-targeted, CaMKII inhibitor based therapies.

REFERENCES

1. Walters, A. M., G. A. Porter, Jr., and P. S. Brookes, Mitochondria as a drug target in ischemic heart disease and cardiomyopathy. Circ Res, 2012. 111(9): p. 1222-36.
2. Erickson, J. R., M. A. Joiner, X. Guan, W. Kutschke, J. Yang, C. V. Oddis, R. K. Bartlett, J. S. Lowe, S. E. O'Donnell, N. Aykin-Burns, M. C. Zimmerman, K. Zimmerman, A.-J. L. Ham, R. M. Weiss, D. R. Spitz, M. A. Shea, R. J. Colbran, P. J. Mohler, and M. E. Anderson, A dynamic pathway for calcium-independent activation of CaMKII by methionine oxidation. Cell, 2008. 133(3): p. 462-474.
3. Yang, Y., W.-Z. Zhu, M. Joiner, R. Zhang, C. V. Oddis, Y. Hou, J. Yang, E. E. Price, L. Gleaves, M. Eren, G. Ni, D. E. Vaughan, R.-P. Xiao, and M. E. Anderson, Calmodulin kinase II inhibition protects against myocardial cell apoptosis in vivo. Am. J. Physiol. Heart Circ. Physiol., 2006. 291(6): p. H3065-H3075.
4. Joiner, M. L., O. M. Koval, J. Li, B. J. He, C. Allamargot, Z. Gao, E. D. Luczak, D. D. Hall, B. D. Fink, B. Chen, J. Yang, S. A. Moore, T. D. Scholz, S. Strack, P. J. Mohler, W. I. Sivitz, L. S. Song, and M. E. Anderson, CaMKII determines mitochondrial stress responses in heart. Nature, 2012. 491(7423): p. 269-73.
5. Zhang, T., L. S. Maier, N. D. Dalton, S. Miyamoto, J. Ross, Jr, D. M. Bers, and J. H. Brown, The {delta}C Isoform of CaMKII Is Activated in Cardiac Hypertrophy and Induces Dilated Cardiomyopathy and Heart Failure. Circ Res, 2003. 92(8): p. 912-919.
6. Odagiri, K., H. Katoh, H. Kawashima, T. Tanaka, H. Ohtani, M. Saotome, T. Urushida, H. Satoh, and H. Hayashi, Local control of mitochondrial membrane potential, permeability transition pore and reactive oxygen species by calcium and calmodulin in rat ventricular myocytes. Journal of Molecular and Cellular Cardiology, 2009. 46(6): p. 989-997.
7. Zhang, R., M. S. C. Khoo, Y. Wu, Y. Yang, C. E. Grueter, G. Ni, E. E. Price, W. Thiel, S. Guatimosim, L.-S. Song, E. C. Madu, A. N. Shah, T. A. Vishnivetskaya, J. B. Atkinson, V. V. Gurevich, G. Salama, W. J. Lederer, R. J. Colbran, and M. E. Anderson, Calmodulin kinase II inhibition protects against structural heart disease. Nature Medicine, 2005. 11(43): p. 409-417.
8. Kroemer, G. and J. C. Reed, Mitochondrial control of cell death. Nature Medicine, 2000. 6(5): p. 513-519.
9. Clapham, D. E., Calcium Signaling. Cell, 2007. 131(6): p. 1047-1058.
10. Singh, M. V., A. Kapoun, L. Higgins, W. Kutschke, J. M. Thurman, R. Zhang, M. Singh, J. Yang, X. Guan, J. S. Lowe, R. M. Weiss, K. Zimmermann, F. E. Yull, T. S. Blackwell, P. J. Mohler, and M. E. Anderson, Ca2+/calmodulin-dependent kinase II triggers cell membrane injury by inducing complement factor B gene expression in the mouse heart. J. Clin. Invest., 2009. 119(4): p. 986-996.
11. Hakem, R., A. Hakem, G. S. Duncan, J. T. Henderson, M. Woo, M. S. Soengas, A. Elia, J. L. de la Pompa, D. Kagi, W. Khoo, J. Potter, R. Yoshida, S. A. Kaufman, S. W. Lowe, J. M. Penninger, and T. W. Mak, Differential requirement for caspase 9 in apoptotic pathways in vivo. Cell, 1998. 94(3): p. 339-352.
12. Olichon, A. I., L. Baricault, N. Gas, E. Guillou, A. Valette, P. Belenguer, and G. Lenaers, Loss of OPA1 perturbates the mitochondrial inner membrane structure and integrity, leading to cytochrome c release and apoptosis. J. Biol. Chem., 2003. 278(10): p. 7743-7746.
13. Chao, L. H., P. Pellicena, S. Deindl, L. A. Barclay, H. Schulman, and J. Kuriyan, Intersubunit capture of regulatory segments is a component of cooperative CaMKII activation. Nat Struct Mol Biol, 2010. 17(3): p. 264-72.
14. Coultrap, S. J. and K. U. Bayer, Improving a natural CaMKII inhibitor by random and rational design. PLoS One, 2011. 6(10): p. e25245.
15. Zhang, X. Q., J. Intra, and A. K. Salem, Conjugation of polyamidoamine dendrimers on biodegradable microparticles for nonviral gene delivery. Bioconjugate Chemistry, 2007. 18(6): p. 2068-2076.
16. Hong, L., Y. Krishnamachari, D. Seabold, V. Joshi, G. Schneider, and A. K. Salem, Intracellular Release of 17-beta Estradiol from Cationic Polyamidoamine Dendrimer Surface-Modified Poly (Lactic-co-Glycolic Acid) Microparticles Improves Osteogenic Differentiation of Human Mesenchymal Stromal Cells. Tissue Engineering Part C-Methods, 2011. 17(3): p. 319-325.
17. Sakhalkar, H. S., M. K. Dalai, A. K. Salem, R. Ansari, A. Fu, M. F. Kiani, D. T. Kurjiaka, J. Hanes, K. M. Shakesheff, and D. J. Goetz, Leukocyte-inspired biodegradable particles that selectively and avidly adhere to inflamed endothelium in vitro and in vivo. Proceedings of the National Academy of Sciences of the United States of America, 2003. 100(26): p. 15895-15900.
18. Zhang, X. Q., C. E. Dahie, G. J. Weiner, and A. K. Salem, A comparative study of the antigen-specific immune response induced by co-delivery of CpG ODN and antigen using fusion molecules or biodegradable microparticles. J Pharm Sci, 2007. 96(12): p. 3283-92.
19. Abbas, A. O., M. D. Donovan, and A. K. Salem, Formulating poly(lactide-co-glycolide) particles for plasmid DNA delivery. Journal of Pharmaceutical Sciences, 2008. 97(7): p. 2448-2461.
20. Zhang, X. Q., J. Intra, and A. K. Salem, Comparative study of poly (lactic-co-glycolic acid)-poly ethyleneimine-plasmid DNA microparticles prepared using double emulsion methods. Journal of Microencapsulation, 2008. 25(1): p. 1-12.
21. Intra, J. and A. K. Salem, Rational design, fabrication, characterization and in vitro testing of biodegradable microparticles that generate targeted and sustained transgene expression in HepG2 liver cells. Journal of Drug Targeting, 2011. 19(6): p. 393-408.
22. Hong, L., N. Wei, V. Joshi, Y. Yu, N. Kim, Y. Krishnamachari, Q. Zhang, and A. K. Salem, Effects of Glucocorticoid Receptor Small Interfering RNA Delivered Using Poly Lactic-Co-Glycolic Acid Microparticles on Proliferation and Differentiation Capabilities of Human Mesenchymal Stromal Cells. Tissue Engineering Part A, 2012. 18(7-8): p. 775-784.
23. Joshi, V. B., S. M. Geary, B. R. Carrillo-Conde, B. Narasimhan, and A. K. Salem, Characterizing the antitumor response in mice treated with antigen-loaded polyanhydride microparticles. Acta Biomaterialia, 2013. 9(3): p. 5583-5589.
24. Joshi, V. B., S. M. Geary, B. R. Carrillo-Conde, B. Narasimhan, and A. K. Salem, Characterizing the antitumor response in mice treated with antigen-loaded polyanhydride microparticles. Acta Biomater, 2013. 9(3): p. 5583-9.
25. Salem, A. K., S. M. Cannizzaro, M. C. Davies, S. J. B. Tendler, C. J. Roberts, P. M. Williams, and K. M. Shakesheff, Synthesis and characterisation of a degradable poly (lactic acid)-poly(ethylene glycol) copolymer with biotinylated end groups. Biomacromolecules, 2001. 2(2): p. 575-580.
26. Salem, A. K., F. R. A. J. Rose, R. O. C. Oreffo, X. B. Yang, M. C. Davies, J. R. Mitchell, C. J. Roberts, S. Stolnik-Trenkic, S. J. B. Tendler, P. M. Williams, and K. M. Shakesheff, Porous polymer and cell composites that self-assemble in situ. Advanced Materials, 2003. 15(3): p. 210-+.
27. Salem, A. K., J. Chao, K. W. Leong, and P. C. Searson, Receptor-mediated self-assembly of multi-component magnetic nanowires. Advanced Materials, 2004. 16(3): p. 268-+.
28. Krishnamachari, Y., M. E. Pearce, and A. K. Salem, Self-assembly of cell-microparticle hybrids. Advanced Materials, 2008. 20(5): p. 989-+.
29. Sinclair, J. and A. K. Salem, Rapid localized cell trapping on biodegradable polymers using cell surface derivatization and microfluidic networking. Biomaterials, 2006. 27(9): p. 2090-4.
30. Lemke, C. D., S. M. Geary, V. B. Joshi, and A. K. Salem, Antigen-coated poly alpha-hydroxy acid based microparticles for heterologous prime-boost adenovirus based vaccinations. Biomaterials, 2013. 34(10): p. 2524-9.
31. Yoo, J., S. R. D'Mello, T. Graf, A. K. Salem, and N. B. Bowden, Synthesis of the first poly(diaminosulfide)s and an investigation of their applications as drug delivery vehicles. Macromolecules, 2012. 45(2): p. 688-697.
32. Salem, A. K., P. C. Searson, and K. W. Leong, Multifunctional nanorods for gene delivery. Nature Materials, 2003. 2(10): p. 668-671.
33. Kim, N., D. H. Jiang, A. M. Jacobi, K. A. Lennox, S. D. Rose, M. A. Behike, and A. K. Salem, Synthesis and characterization of mannosylated pegylated polyethylenimine as a carrier for siRNA. International Journal of Pharmaceutics, 2012. 427(1): p. 123-133.
34. Boddapati, S. V., G. G. D'Souza, and V. Weissig, Liposomes for drug delivery to mitochondria. Methods Mol Biol, 2010. 605: p. 295-303.
35. Boddapati, S. V., G. G. D'Souza, S. Erdogan, V. P. Torchilin, and V. Weissig, Organelle-targeted nanocarriers: specific delivery of liposomal ceramide to mitochondria enhances its cytotoxicity in vitro and in vivo. Nano Letters, 2008. 8(8): p. 2559-63.
36. Marrache, S. and S. Dhar, Engineering of blended nanoparticle platform for delivery of mitochondria-acting therapeutics. Proc Natl Acad Sci USA, 2012. 109(40): p. 16288-93.
37. Biswas, S., N. S. Dodwadkar, A. Piroyan, and V. P. Torchilin, Surface conjugation of triphenylphosphonium to target poly(amidoamine) dendrimers to mitochondria. Biomaterials, 2012. 33(18): p. 4773-82.
38. Tyurina, Y. Y., M. A. Tungekar, M. Y. Jung, V. A. Tyurin, J. S. Greenberger, D. A. Stoyanovsky, and V. E. Kagan, Mitochondria targeting of non-peroxidizable triphenylphosphonium conjugated oleic acid protects mouse embryonic cells against apoptosis: role of cardiolipin remodeling. FEBS Lett, 2012. 586(3): p. 235-41.
39. Jiang, J., D. A. Stoyanovsky, N. A. Belikova, Y. Y. Tyurina, Q. Zhao, M. A. Tungekar, V. Kapralova, Z. Huang, A. H. Mintz, J. S. Greenberger, and V. E. Kagan, A mitochondrial-targeted triphenylphosphonium-conjugated nitroxide functions as a radioprotector/mitigator. Radiat Res, 2009. 172(6): p. 706-17.
40. Zordoky, B. N. M. and A. O. S. El-Kadi, H9c2 cell line is a valuable in vitro model to study the drug metabolizing enzymes in the heart. Journal of Pharmacological and Toxicological Methods, 2007. 56(3): p. 317-322.
41. Liu, J., R. Kesiry, S. M. Periyasamy, D. Malhotra, Z. J. Xie, and J. I. Shapiro, Ouabain induces endocytosis of plasmalemmal NaK-ATPase in LLC-PKI cells by a clathrin-dependent mechanism. Kidney International, 2004. 66(1): p. 227-241.
42. Jiang, D. H. and A. K. Salem, Optimized dextran-polyethylenimine conjugates are efficient non-viral vectors with reduced cytotoxicity when used in serum containing environments. International Journal of Pharmaceutics, 2012. 427(1): p. 71-79.
43. Krishnamachari, Y. and A. K. Salem, Innovative strategies for co-delivering antigens and CpG oligonucleotides. Advanced Drug Delivery Reviews, 2009. 61(3): p. 205-217.
44. Petushkov, A., J. Intra, J. B. Graham, S. C. Larsen, and A. K. Salem, Effect of Crystal Size and Surface Functionalization on the Cytotoxicity of Silicalite-1 Nanoparticles. Chemical Research in Toxicology, 2009. 22(7): p. 1359-1368.
45. Clapper, J. D., M. E. Pearce, C. A. Guymon, and A. K. Salem, Biotinylated biodegradable nanotemplated hydrogel networks for cell interactive applications. Biomacromolecules, 2008. 9(4): p. 1188-94.
46. Zhang, G. X., X. M. Lu, S. Kimura, and A. Nishiyama, Role of mitochondria in angiotensin II-induced reactive oxygen species and mitogen-activated protein kinase activation. Cardiovasc Res, 2007. 76(2): p. 204-12.
47. Halestrap, A. P., What is the mitochondrial permeability transition pore? Journal of Molecular and Cellular Cardiology, 2009. 46(6): p. 821-831.
48. Baughman, J. M., F. Perocchi, H. S. Girgis, M. Plovanich, C. A. Belcher-Timme, Y. Sancak, X. R. Bao, L. Strittmatter, O. Goldberger, R. L. Bogorad, V. Koteliansky, and V. K. Mootha, Integrative genomics identifies MCU as an essential component of the mitochondrial calcium uniporter. Nature, 2011. 476(7360): p. 341-5.
49. Miyawaki, A., J. Llopis, R. Heim, J. M. McCaffery, J. A. Adams, M. Ikura, and R. Y. Tsien, Fluorescent indicators for Ca2+ based on green fluorescent proteins and calmodulin. Nature, 1997. 388(6645): p. 882-887.

Example 2

Preparation of PLGA-CTAB Nanoparticles

Nanoparticles were prepared via a water/oil/water double emulsion that included polylactic-co-glycolic acid (PLGA) and cetyltrimethylammonium bromide (CTAB) under a variety of experimental conditions. The nanoparticles thus prepared were tested for uptake by H9C2 cells.

Figure 7:
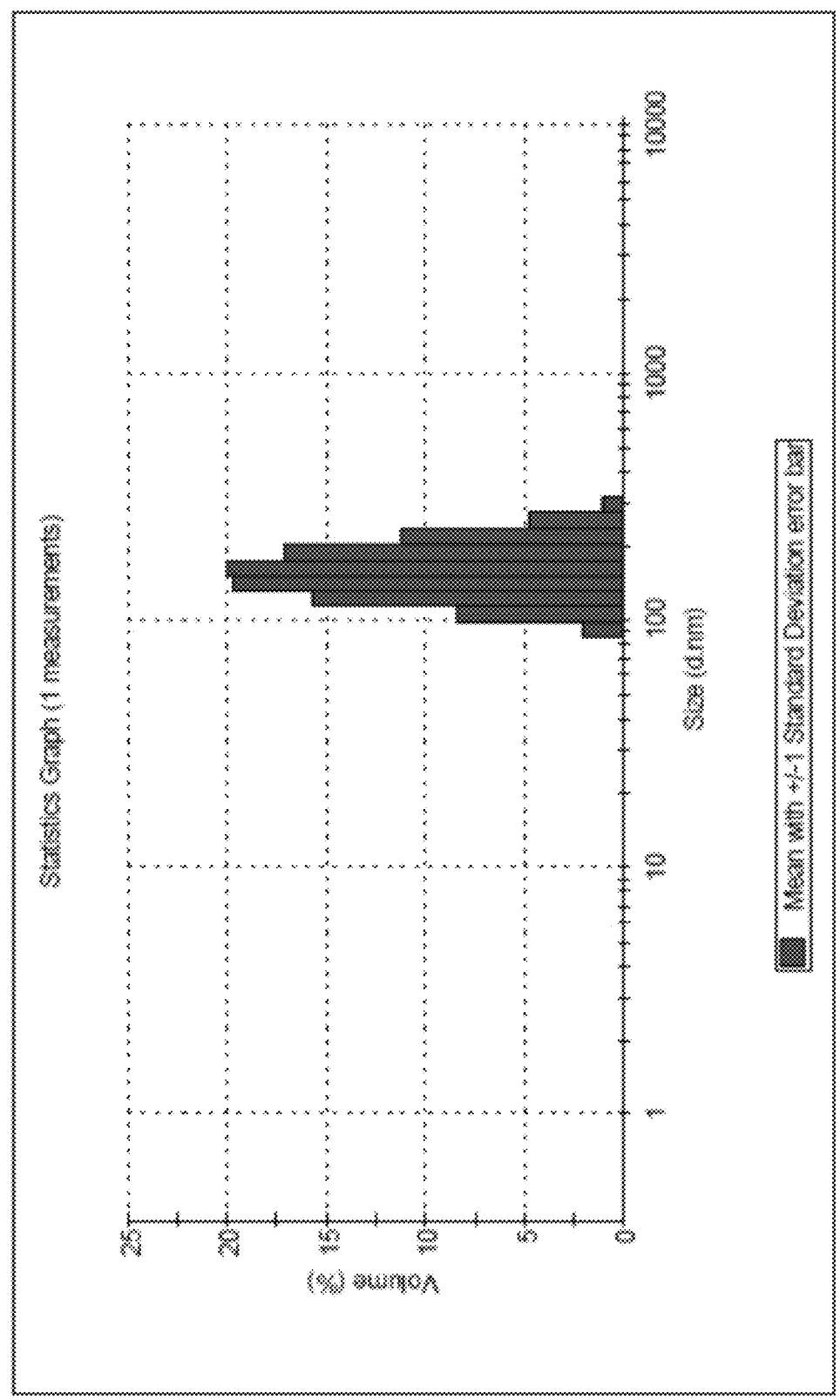
FIG. 7 illustrates the size distribution of nanoparticles prepared according to one embodiment contemplated herein.
Figure 8:
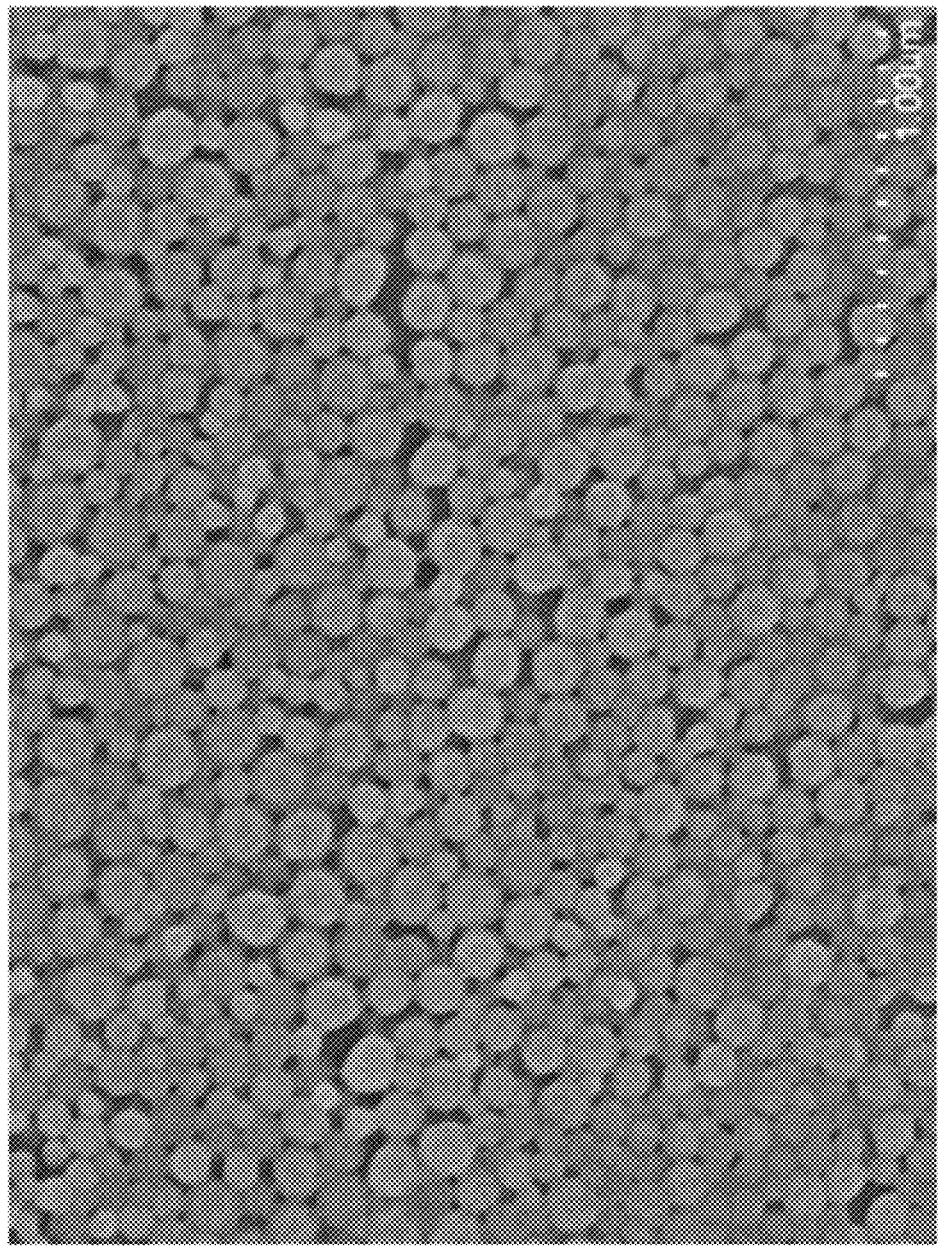
FIG. 8 provides a scanning electron micrograph (SEM) image of nanoparticles prepared according to one embodiment contemplated herein.

Experiment (1) A first aqueous solution (W1) was prepared (W1: 100 µl of 1% CTAB in PBS) and an Oil solution was prepared (Oil: 100 mg of PLGA in 2 ml dichloromethane (DCM). The W1 solution and the Oil solution were combined and sonicated for 45 seconds to form an emulsion. A second aqueous was prepared (W2: 8 ml of 1% CTAB) and was added to the emulsion. The emulsion was sonicated again for 45 seconds. After sonication, 22 ml of 1% CTAB was added and the emulsion was stirred via a magnetic stirring device at a speed setting of 6.5. The emulsion was centrifuged (2000 rpm, 5 minutes, 1 acc) and the supernatant was retained and subsequently centrifuged (8500 rpm. 15-20 minutes, 1 acc). The precipitate was washed 1× with 30 ml of purified water and the size of the nanoparticles thus obtained was assessed by SEM. (See FIG. 7; Mean diameter=170.0 nm; Pdi=0.172).

Experiment (2) Nanoparticles were prepared as in Experiment (1) except that Rhodamine-B (0.5 mg) was added to the Oil solution. The particles thus obtained were assessed by SEM.

Experiment (3) The nanoparticles of Experiment (2) were tested for uptake by H9C2 cells. On Day 1, cells were seeded at $5\times10^4$ cells/500 μl/well. On Day 2, the media was aspirated and a mixture of fresh media (500 μl) plus nanoparticles in PBS (100 μl) were added. As a control, PBS (100 μl) alone was added. On Day 3, DRAQ5™ dye (Thermo Fisher Scientific) and MitoTracker Green FM dye (Life Technologies) were added per manufacturers' instructions and live cell fluorescence imaging was performed using a Zeiss LSM 510 inverted microscope to detect cellular uptake of the nanoparticles. DRAQ5™ dye is localized to nuclei whereas MitoTracker Green FM dyez is localized to mitochondria.

Experiment (4) Nanoparticles were prepared as in Experiment (1) except that Rhodamine-B (30 mg) or coumarin (10 mg) was added to the Oil solution. The size of the particles thus obtained was assessed by SEM. (Rhodamine particles: Mean diameter (nm)=166.0; Pdi=0.276; Zeta Potential (mV)=−11.5. Coumarin particles: Mean diameter (nm)=366.0; Pdi=0.348; Zeta Potential (mV)=3.29).

Experiment (5) Nanoparticles were prepared as in Experiment (1) except that coumarin (3 mg) was added to the Oil solution. The emulsion was centrifuged (2000 rpm, 5 minutes, 1 acc) and the supernatant was retained and subsequently centrifuged (8500 rpm. 15-20 minutes, 1 acc). The precipitate was washed 1× with 30 ml ultrapure water or was washed 3× using an Amicon Ultra-15 centrifugal filter unit (10,000 MWCO; 3000*g; 30 minutes). The size of the particles thus obtained was assessed by SEM. (Particles in supernatant after centrifugation at 2000 rpm: Mean diameter (nm)=154.0; Pdi=0.187. Particles after centrifugation at 8500 rpm and washing 1× with 30 ml ultrapure water: Mean diameter (nm)=155.3; Pdi=0.245. Particles after centrifugation at 8500 rpm and washing 3× using an Amicon Ultra-15 centrifugal filter unit: Mean diameter (nm)=152.2; Pdi=0.286).

Figure 9:
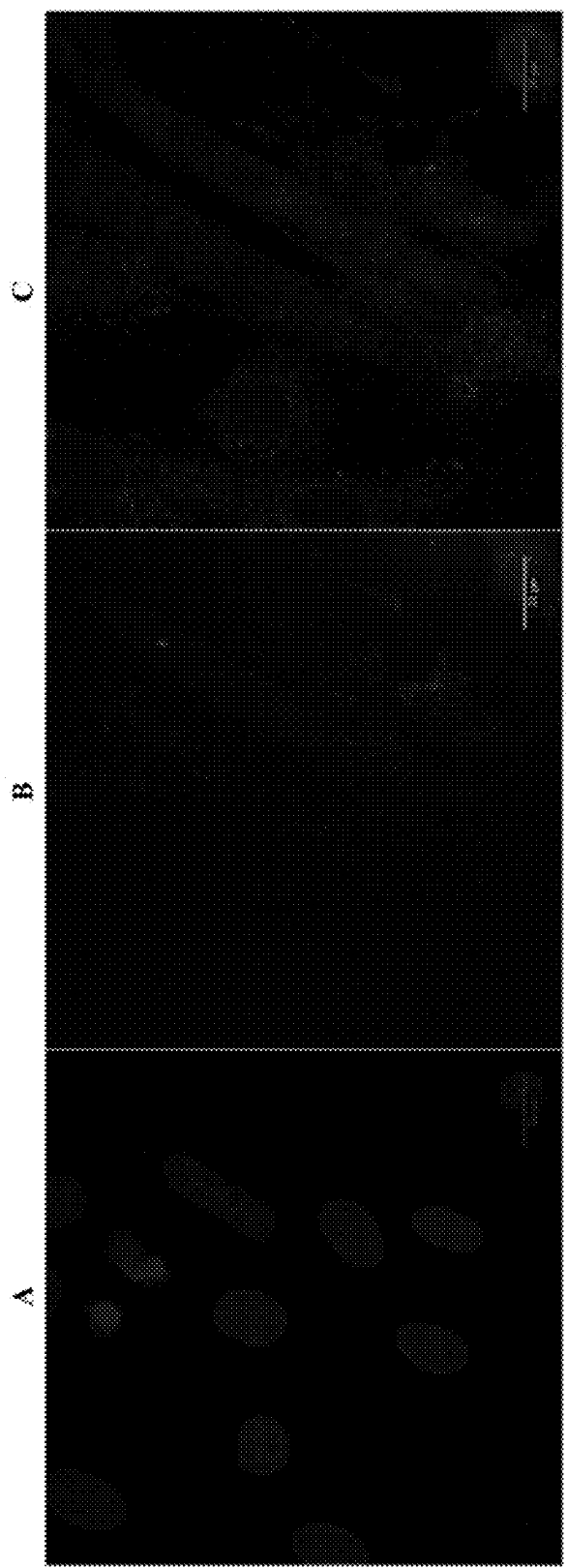
FIG. 9 illustrates cellular uptake of nanoparticles loaded with 3 mg Coumarin. Cells were stained with a nucleic specific stain and a mitochondria specific stain. Panel A) nuclei; Panel B) Coumarin; Panel C) mitochondria.

Experiment (6) The nanoparticles of Experiment (5) after centrifugation at 8500 rpm and washing 1× with 30 ml ultrapure water were tested for cellular uptake by H9C2 cells by the method of Experiment (3). Results are shown in FIG. 9, Panel A (nuclei); Panel B (coumarin); Panel C (mitochondria). The nanoparticles were observed to be taken up by the H9C2 cells despite lacking a surface ligand.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

---

We claim:

1. Cationic biodegradable nanoparticles comprising:
   (a) a mixture of polylactic-co-glycolic acid (PLGA) and polyamidoamine (PAMAM) dendrimers at a ratio between 6:1 and 2:1 by mass, wherein the nanoparticles have a zeta-potential between about 5-45 mV;
   (b) a CaMKII inhibitor; and
   (c) a mitochondrial location sequence (MLS) peptide conjugated to the nanoparticles.

2. The nanoparticles of claim 1, wherein the nanoparticles further comprise a cationic surfactant.

3. The nanoparticles of claim 2, wherein the cationic surfactant is a quaternary ammonium compound.

4. The nanoparticles of claim 1, wherein the nanoparticles have an average diameter between about 25 nm and 500 nm.

5. The nanoparticles of claim 1, wherein the CaMKII inhibitor is a peptide.

6. The nanoparticles of claim 5, wherein the peptide comprises an amino acid sequence KRPPKLGQIGRAKRVVIEDDR (SEQ ID NO:1).

7. The nanoparticles of claim 1, wherein the CAMKII inhibitor is KN-93.

8. The nanoparticles of claim 1, wherein the CaMKII inhibitor is an aryl-indolyl maleimide.

9. The nanoparticles of claim 1, wherein the MLS peptide comprises an amino acid sequence MSVLTPLLLRGLTGSARRLPVPRAKIHSLL (SEQ ID NO:2).

10. A pharmaceutical composition comprising the nanoparticles of claim 1.

11. The pharmaceutical composition of claim 10 formulated for intravenous delivery.

* * * * *